(12) United States Patent
Jarausch

(10) Patent No.: US 11,464,997 B2
(45) Date of Patent: Oct. 11, 2022

(54) SYSTEMS AND METHODS FOR LIGHT GENERATION AND USE THEREOF

(71) Applicant: Konrad Jarausch, Albany, CA (US)

(72) Inventor: Konrad Jarausch, Albany, CA (US)

(*) Notice: Subject to any disclaimer, the term of this patent is extended or adjusted under 35 U.S.C. 154(b) by 16 days.

(21) Appl. No.: 16/932,710

(22) Filed: Jul. 18, 2020

(65) Prior Publication Data

US 2022/0016437 A1  Jan. 20, 2022

(51) Int. Cl.
*A61N 5/06* (2006.01)
*A61L 2/24* (2006.01)
*A61L 2/10* (2006.01)

(52) U.S. Cl.
CPC .............. *A61N 5/0616* (2013.01); *A61L 2/10* (2013.01); *A61L 2/24* (2013.01); *A61N 5/0618* (2013.01); *A61L 2202/11* (2013.01); *A61L 2202/14* (2013.01); *A61N 2005/0626* (2013.01); *A61N 2005/0642* (2013.01); *A61N 2005/0661* (2013.01)

(58) Field of Classification Search
CPC ............. A61N 5/0616; A61N 5/0618; A61N 2005/0626; A61N 2005/0642; A61N 2005/0661; A61L 2/10; A61L 2/24; A61L 2202/11; A61L 2202/14
USPC ............................................... 607/88
See application file for complete search history.

(56) References Cited

U.S. PATENT DOCUMENTS 5,358,503 A * 10/1994 Bertwell ............. A61N 5/0616
606/2

5,892,619 A  4/1999  Chubb et al.
6,016,038 A  1/2000  Mueller et al.
(Continued)

FOREIGN PATENT DOCUMENTS

AU  2017265107 B2  7/2019
CA  2638508 C  2/2010
(Continued)

OTHER PUBLICATIONS

"Our Light Science: The Benefits of the Sun Without the Harmful Rays," [online], [retrieved Aug. 2, 2020] <URL: https://www.solius.com/> (9pgs).
(Continued)

*Primary Examiner* — Carl H Layno
*Assistant Examiner* — Michael J Lau
(74) *Attorney, Agent, or Firm* — Ali Uyanik

(57) ABSTRACT

System and methods to generate and control light for use in therapeutic, aesthetic, disinfection, and other light-related applications in settings where a significant portion of skin is exposed to light (e.g., shower, sauna, locker-room). Characteristics of the light are controlled to simulate specific spectra of natural sunlight and unnatural light and deliver targeted doses of UV light (e.g., for vitamin-D synthesis, boosting the immune system, tanning), UV-C light (e.g., to kill bacteria, viruses, and fungi), visible light (e.g., to anchor a circadian rhythm to improve mood, metabolism, cognitive functions, physical performance, and sleep), and red or infrared light (e.g., for skin rejuvenation, wound healing, tissue repair, blood-flow, muscle recovery, circulation) while, at the same time, minimizing negative impacts of light exposure. Various embodiments may further create the experience of an outdoor shower.

20 Claims, 31 Drawing Sheets

(56) References Cited

U.S. PATENT DOCUMENTS

| | | | |
|---|---|---|---|
| 6,851,814 B2 | 2/2005 | Chubb et al. | |
| 6,887,260 B1* | 5/2005 | McDaniel | A61P 17/10 |
| | | | 607/91 |
| 7,824,065 B2 | 11/2010 | Maxik | |
| 8,647,373 B1 | 2/2014 | Shepherd et al. | |
| 8,938,295 B2 | 1/2015 | Baird et al. | |
| 9,061,082 B2 | 6/2015 | Gaska et al. | |
| 9,744,378 B2 | 8/2017 | Tapper et al. | |
| 9,795,000 B1* | 10/2017 | Sooch | H05B 47/16 |
| 9,931,171 B1* | 4/2018 | Peyman | A61B 3/14 |
| 10,235,033 B2 | 3/2019 | Laflamme et al. | |
| 2002/0198575 A1* | 12/2002 | Sullivan | A61N 5/0616 |
| | | | 607/91 |
| 2003/0125782 A1* | 7/2003 | Streeter | A61N 5/0616 |
| | | | 604/20 |
| 2004/0030371 A1* | 2/2004 | Barghelame | A61H 33/06 |
| | | | 607/96 |
| 2006/0276860 A1* | 12/2006 | Ferren | A61K 8/046 |
| | | | 606/9 |
| 2007/0038206 A1* | 2/2007 | Altshuler | A46B 15/0036 |
| | | | 606/20 |
| 2008/0091250 A1* | 4/2008 | Powell | H05B 45/20 |
| | | | 607/90 |
| 2009/0216299 A1* | 8/2009 | Dantus | A61N 5/0616 |
| | | | 385/27 |
| 2010/0017953 A1* | 1/2010 | O'Keeffe | A61N 5/0625 |
| | | | 219/480 |
| 2010/0174222 A1* | 7/2010 | McDaniel | A61K 41/0057 |
| | | | 424/59 |
| 2013/0172963 A1* | 7/2013 | Moffat | A61N 5/0616 |
| | | | 607/94 |
| 2013/0231719 A1* | 9/2013 | Soltesz-Nagy | H01J 61/40 |
| | | | 607/88 |
| 2014/0288351 A1* | 9/2014 | Jones | A61N 5/0624 |
| | | | 607/90 |
| 2015/0134032 A1 | 5/2015 | Chicchi et al. | |
| 2015/0174425 A1* | 6/2015 | Toyos | A61N 5/0616 |
| | | | 606/127 |
| 2016/0016001 A1* | 1/2016 | Loupis | H05B 45/20 |
| | | | 604/20 |
| 2016/0220834 A1* | 8/2016 | Schwarz | A61N 2/002 |
| 2016/0296650 A1* | 10/2016 | Liao | A61L 2/10 |
| 2017/0225006 A1* | 8/2017 | Anderson | A61K 9/06 |
| 2017/0231058 A1* | 8/2017 | Sadwick | H05B 45/18 |
| 2017/0239489 A1* | 8/2017 | Bourke, Jr. | A61N 5/062 |
| 2017/0246329 A1* | 8/2017 | Lloyd | A61L 2/084 |
| 2018/0280721 A1* | 10/2018 | Beckner | A61B 5/0532 |
| 2019/0030359 A1* | 1/2019 | Dijkstra | A61B 5/444 |
| 2019/0126060 A1* | 5/2019 | Dijkstra | F21V 33/0004 |
| 2019/0209806 A1* | 7/2019 | Allen | H04L 12/282 |
| 2019/0329064 A1* | 10/2019 | Lee | A61N 5/0613 |
| 2019/0357976 A1* | 11/2019 | Youngquist | A61B 18/20 |
| 2020/0030626 A1* | 1/2020 | Müller | A61N 5/0616 |
| 2020/0114164 A1* | 4/2020 | Bourke, Jr. | A61N 5/025 |
| 2020/0121944 A1 | 4/2020 | Strahan et al. | |
| 2020/0178892 A1* | 6/2020 | Maslik | A61B 5/4836 |

FOREIGN PATENT DOCUMENTS

| | | |
|---|---|---|
| DE | 102007032585 A1 | 1/2009 |
| EP | 2164568 B1 | 2/2016 |
| ES | 2656893 | 7/2013 |
| JP | 2003297105 A | 10/2003 |
| JP | 2008508918 A | 3/2008 |
| WO | 2012011013 A2 | 1/2012 |
| WO | 2014036133 A1 | 3/2014 |
| WO | 2015116833 A1 | 8/2015 |
| WO | 2019195816 A1 | 10/2019 |
| WO | 2020131235 A1 | 6/2020 |

OTHER PUBLICATIONS

"Sperti Vitamin D Sunlamp," [online], [retrieved Aug. 2, 2020] <URL: https://www.solius.com/> (4pgs).

Liszewski, Feb. 10, 2020, "Mitsubishi's Fake LED Skylights Simulate Sunlight to Make Offices Feel Less Depressing," [online], [retireved Aug. 2, 2020] <URL: https://gizmodo.com/mitsubishi-s-fake-led-skylights-simulate-sunlight-to-ma-1841573763/> (6pgs).

"Red and Infrared LED Light Therapy Devices—Joovv," [online], [retrieved Aug. 2, 2020] <URL: https://www.solius.com/> (14pgs).

Kalajian et al. "Ultraviolet B Light Emitting Diodes (LEDs) Are More Efficient and Effective in Producing Vitamin D3 in Human Skin Compared to Natural Sunlight," in Scientific Reports,Published online 2017 [online], [retireved Aug. 2, 2020] <URL: https://www.researchgate.netpublication/319683521_Ultraviolet_B_Light_Emitting_Diodes_LEDs_Are_More_Efficient_and_Effective_in_Producing_Vitamin_D3_in_Human_Skin_Compared_to_Natural_Sunlight > (8pgs).

* cited by examiner

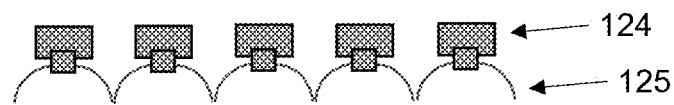
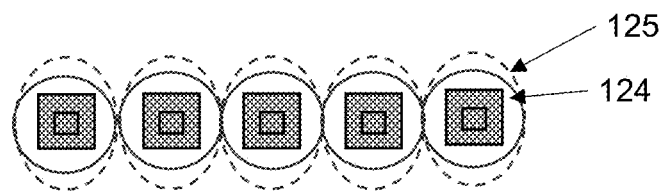
FIG. 3A
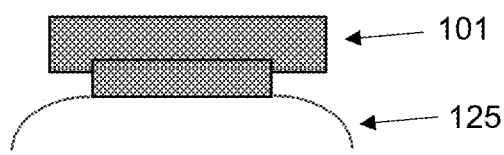
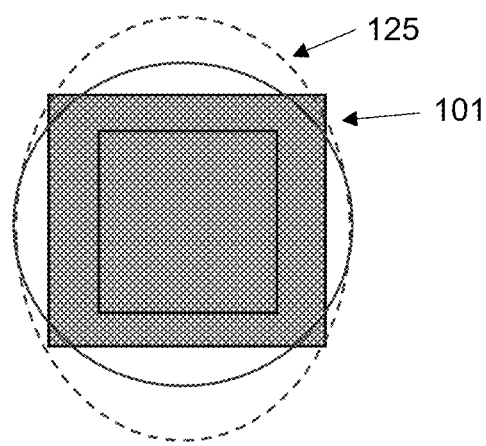
FIG. 3B

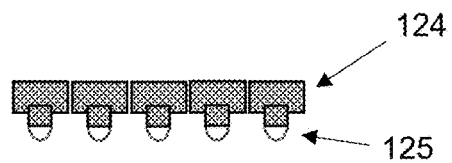
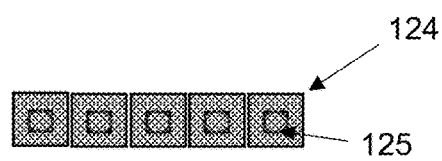
FIG. 3C
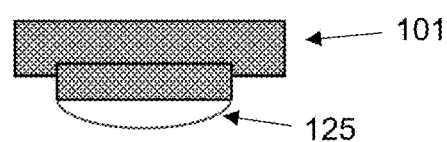
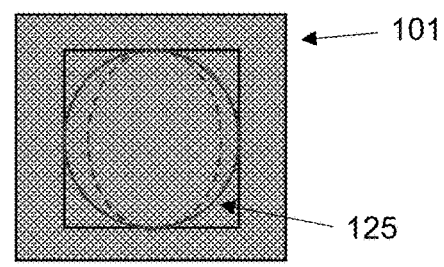
FIG. 3D

CHANGING FOCAL LENGTH OF LIGHT

CHANGING FOCAL LENGTH OF LIGHT

500
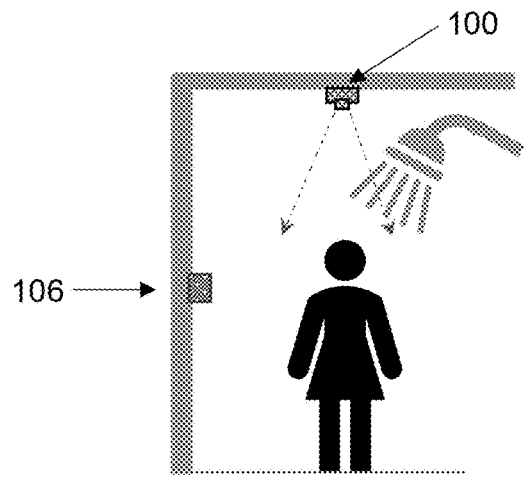
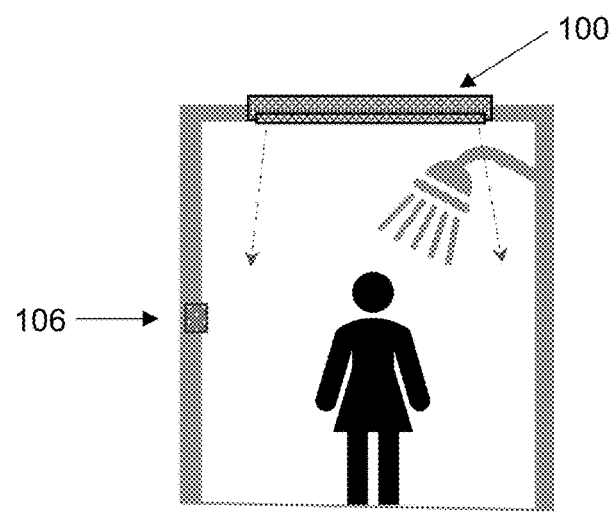
FIG. 5A
FIG. 5B
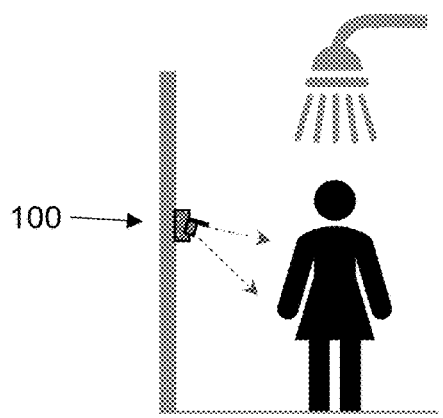
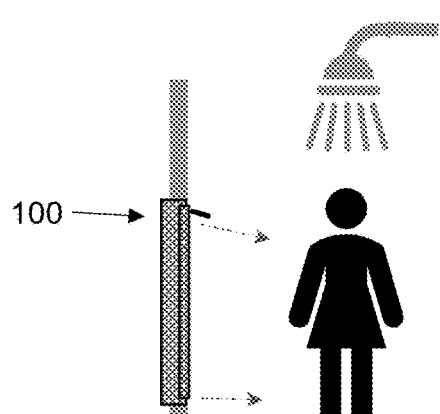
FIG. 5C
FIG. 5D

600

SYSTEMS AND METHODS FOR LIGHT GENERATION AND USE THEREOF

BACKGROUND

A. Technical Field

The present disclosure relates generally to systems and methods for generating and using light. More particularly, the present disclosure relates to systems and methods for generating and controlling light having various spectra for therapeutic, aesthetic, disinfection, and other applications.

B. Background

Daily exposure to sunlight is known to improve health and wellness and significantly reduces the risk of chronic diseases such as depression and diabetes. Sunlight interacts with living organisms in ways that are both beneficial (e.g., rejuvenation of skin, vitamin-D synthesis, improving mood) and detrimental (e.g., risk of skin-cancer, skin-aging, retina damage). However, since the composition of light intensities and wavelengths that reach the earth's surface vary significantly with time of day, season, location, and environmental conditions, such as weather patterns, smog, ozone, and nearby reflective surfaces, harnessing the beneficial effects of sunlight, while avoiding harmful interactions presents significant challenges.

Existing approaches for delivering doses of beneficial light use exposure chambers, such as tanning beds, or stand-alone devices, such as seasonal affective disorder (SAD) lamps, which are typically limited to delivering a fixed range of wavelengths of light for a specific treatment or purpose. Such approaches lack the ability to adjust spectral power distribution to according to users' unique needs, or to adapt to individual users' environments. Further, their use oftentimes requires cumbersome user interaction, which impedes seamless integration into users' daily routines and, ultimately, reduces user compliance and thus efficacy.

Accordingly, it is desirable to have systems and methods that can be tailored to create and deliver "on demand" adequate doses of beneficial visible and non-visible light to users to obtain health-related and other effects of sunlight in a safe and controlled manner.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments. Items in the figures are not to scale.

Figure ("FIG.") 1A is a side-view of an exemplary modular light generation and delivery apparatus according to various embodiments of the present disclosure.

FIG. 2I is a plan-view of the apparatus shown in FIG. 2H.

FIG. 3A-3F illustrate optical elements for light sources that generate zones of illumination according to various embodiments of the present disclosure.

FIG. 5A-FIG. 5D and FIG. 6A-FIG. 6D are side-views illustrating installation and use of an exemplary light generation and delivery apparatus in a chamber, according to various embodiments of the present disclosure.

DETAILED DESCRIPTION OF EMBODIMENTS

Figure 1A:
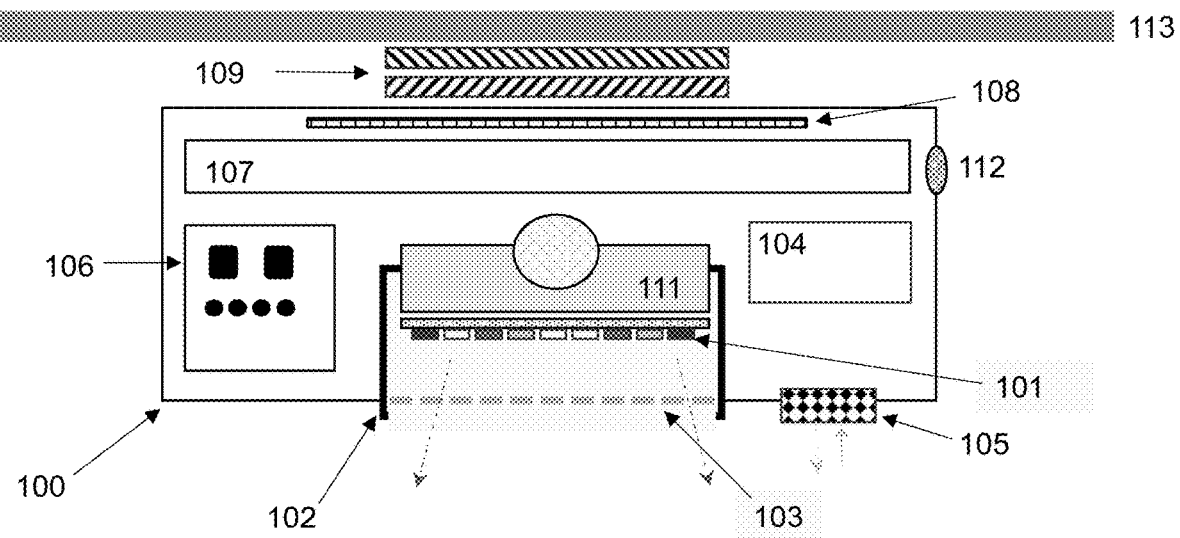
FIG. 1B is a plan-view of an exemplary modular light generation and delivery apparatus comprising a shutter according to various embodiments of the present disclosure.
FIG. 1C is a side-view of an exemplary modular light generation and delivery apparatus comprising a shutter according to various embodiments of the present disclosure.

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled," "connected," or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated.

The terms "include," "including," "comprise," and "comprising" shall be understood to be open terms and any lists the follow are examples and not meant to be limited to the listed items. Any headings used herein are for organizational purposes only and shall not be used to limit the scope of the description or the claims. Each reference mentioned in this patent document is incorporate by reference herein in its entirety.

Furthermore, it shall be noted that embodiments described herein are given in the context of therapeutic, aesthetic, and disinfection applications, but one skilled in the art shall recognize that the teachings of the present disclosure are not limited to such applications and may equally be used in other contexts and environments that may benefit from the systems and methods for generating and using light, including yet to discovered therapeutic benefits of light for the human body.

In this document the term "light source" includes any number and type of light source known in the art. "Apparatus" refers to any number and type of device that comprises such a light source. "Controller" comprises logic elements and other control elements and circuitry recognized by one of skilled in the art. The terms "sunlight" and "natural sunlight" are used interchangeably. Similarly, the terms "retrofit" and "retrofitable" and the terms "Covid-19," "Covid-19-related," and "SARS-CoV-2" are used interchangeably. The term "unnatural light" refers to a set of characteristics of light that does not represent a natural spectral distribution of sunlight. The term "light recipe" refers to a set of conditions or parameters, such as wavelengths, intensities, exposure time and other light-related conditions that are used to simulate one or more spectral distributions of natural sunlight and/or create any combination of custom natural and/or unnatural light exposures to achieve one or more wanted effects, while reducing or eliminating certain unwanted effects. The words "optimal," "optimize," "optimization," and the like refer to an improvement of an outcome or a process and do not require that the specified outcome or process has achieved a maximum or peak state.

FIG. 1A is a side-view of an exemplary modular, battery-driven light generation and delivery apparatus according to various embodiments of the present disclosure. In embodiments, apparatus 100 may comprise light source 101, optical cavity 102, diffuser 103, controller 104, sensor 105, user interface 106, battery 107, wireless charging coil 108, and heat-sink 111. Apparatus 100 may be removably attached to ceiling or wall 113, e.g., by using mounting hardware 109.

In embodiments, apparatus 100 may comprise one or more light sources 101 that may either directly emit light of specific wavelengths or may emit light that is filtered and/or converted into specific wavelengths. It is understood that any suitable number and locations of light sources 101 may be chosen depending on a specific application. Light source 101 represents any light source or combination of light sources, e.g., LEDs, laser light sources, plasma discharge tubes, incandescent bulbs, or other light sources known in the art. As depicted in FIG. 1A, light source 101 may be implemented using a set of controllable LEDs that are disposed on a printed circuit board (PCB).

In operation, apparatus 100 may generate and deliver targeted doses of light of specific wavelengths to the human body and other objects (not shown in FIG. 1A). In embodiments, ranges of wavelengths generated by light source 101 may be controlled by light source 101 itself, e.g., by utilizing narrow band LEDs or lasers, by utilizing conversion materials, such as phosphors or quantum-dots, or by utilizing optical filters. Any number of light sources 101 may be grouped into one or more electrical channels that each may be associated with light emission of a specific wavelength or range of wavelengths. For example, one channel may control the emission of UV-B light having wavelengths ranging from 280 nm to 320 nm, another channel may control the emission of IR light ranging from 700 nm to 1500 nm, and yet another channel may control the emission of visible light ranging from 380 nm to 740 nm. In embodiments, electrical channels may be subdivided into bands within spectral ranges, e.g., a narrower band of UV-B light (e.g., 290 nm to 305 nm) that may support the synthesis of vitamin-D, or a sub-band of visible light (e.g., 450 nm to 490 nm) that may support the stimulation of a user's circadian rhythm.

Using targeted UV-B exposure for vitamin-D synthesis is known to aid in regulating human immune response, advantageously, for example by reducing overly aggressive immune responses that may cause damage. Vitamin-D levels correlate with the regulation and suppression of the inflammatory cytokine response that causes the severe consequences of Covid-19 and "acute respiratory distress syndrome." Thus, UV-B exposure and vitamin-D are directly correlated with Covid mortality. Studies suggest that the active form of vitamin-D enhances the expression of ACE-2 which is a host cell receptor responsible for mediating infection by severe acute respiratory syndrome coronavirus 2 (SARS-CoV-2). In a similar way, high vitamin-D levels correlate with a lower risk for, and reduced expression of autoimmune disorders, such as multiple sclerosis.

Therefore, in embodiments, apparatus 100 may be used to provide a narrow range of photon energies/wavelengths that are tailored to match specific therapeutic pathways. As an example, apparatus 100 may provide a narrow range of UV-B photons to match the action spectrum of pre-vitamin-D synthesis. In such embodiments, by providing photons with a wavelength of 290 nm to 300 nm, light generated by apparatus 100 is over 100 times more effective at vitamin-D synthesis than exposure to natural sunlight that contains over 100 times more photons having wavelengths from 305 nm to 320 nm, which do not meaningfully contribute to pre-vitamin-D synthesis but, instead, are associated with increased risk factors for skin cancers. In embodiments, the resulting increase in efficacy allows apparatus 100 to generate and maintain healthy vitamin-D levels at cumulative UV doses that are 100 to 1000 times lower than the exposure to natural sunlight, thereby, mitigating the risk of skin-aging and skin cancer.

In embodiments, apparatus 100 may be implemented as a "retrofit" device that may be deployed in an existing space, e.g., in a shower, sauna, or gym without the need of providing an external power source or penetrating ceiling or wall structures. In such embodiments, apparatus 100 may be battery-powered by a set of rechargeable or single-use batteries 107 and removably affixed onto a ceiling or wall using mounting hardware 109, such as fasteners, suction-ups, stick-on adhesives, Velcro, or magnets, for example, to allow for convenient removal, recharging, or replacement of battery 107. In embodiments, recharging may be accomplished through wireless charging coil 108 or charging port 112, e.g., a waterproof port that may be used as both a charging port and a communication port.

In embodiments, controller 104 may be implemented as an embedded controller having onboard firmware or as a distributed device to control the operation of light source 101 and, thus, the characteristics of emitted light. Such characteristics may comprise wavelengths, intensity, duration, spectral power distribution, etc., as a function of a set of parameters comprising user data (e.g., health condition, skin pigmentation, etc.), environmental data (e.g., spatial information, reflectivity, etc.), and other information. Controller 104 may comprise integrated circuitry, such as logic, memory, I/O circuitry to support various types of communication using any suitable communication protocol and power conversion electronics to operate any component in apparatus 100.

In embodiments, as described in greater detail below, controller 104 may access and execute predetermined light recipes to recreate or simulate the spectral distribution of sunlight and/or create custom unnatural light exposures to achieve certain therapeutic, aesthetic, and/or disinfection benefits, while minimizing adverse effects of natural sunlight. Controller 104 may accomplish this by providing electrical stimuli to operate light source 101, e.g., by using pulse width modulation (PWM), current control, or any combination thereof to generate light having a set of specific characteristics. Controller 104 may generate electrical output signals to control one or more channels of light source 101, e.g., to modulate the amount, duration, and timing of a specific wavelength of light emitted by light source 101. In embodiments, controller 104 may control the one or more channels to cause apparatus 100 to emit light having a set of characteristics, thereby, controlling overall intensity and duration of the emitted light. As an example, controller 104 may control light source 101 to emit UV-B light having a specific intensity and duration while, at the same time, controlling light source 101 to emit visible or infrared light having a certain intensity and duration.

In embodiments, controller 104 may use information regarding the surroundings of apparatus 100, such as the distance from light source 101 to a given target area, the size of the illumination chamber, measured or estimated light reflected from surrounding objects, such as walls, in addition to information about a therapeutic target dose of light, to control one or more channels of light source 101 to generate light that satisfies, e.g., certain characteristics associated with one or more desired health outcomes.

Controller 104 may control apparatus 100 to generate and deliver light by steady-state exposure of particular wavelengths of light, pulsed/modulated exposure of light (e.g., 0 Hz-100 kHz) or any combination thereof. For example, UV-B and visible light may be delivered at a fixed light intensity, while infrared light may be delivered in a pulsed format that may comprise a square-wave, sine wave, or any other pulse sequence.

In embodiments, controller 104 may integrate inputs with inputs that are related to safety protocols/interlocks and convert certain inputs into modulation and timing steps for light source 101. In embodiments, controller 104 may modulate wavelengths of light and/or cause apparatus 100 to deliver spectral power distributions of light as a function of time-of-day.

For example, in the visible spectrum, controller 104 may adjust relative intensities of light source 101 to generate light having a "blue-rich" spectrum (e.g., 10% or more of visible light intensity in the 460 nm to 490 nm wavelength range) in the morning (e.g., between 6:00 am and 1:00 pm) and generate light that has a "blue-free" spectrum (e.g., less than 2% of visible light intensity in the 460 nm to 490 nm range) in the evenings or at night. Similarly, controller 104 may be configured to deliver UV-C light at specific times, e.g., between 2:00 am and 4:00 am when no persons are expected to be in the vicinity of apparatus 101. In embodiments, controller 104 may comprise a real-time clock to adjust light recipes as a function of the time-of-day or time-of-year, for example, to simulate longer days in the summer than in the winter.

In embodiments, controller 104 may accept override commands, e.g., via user interface 106 and may use external commands and/or communicate with external devices, e.g., via bidirectional links. Controller 104 may communicate wired or wirelessly with sensors 105, such as occupancy, facial/eye-recognition, skin-tone, motion, interlock, facial recognition sensors, and with user interface 106, which may be implemented internal or external to apparatus 100. For example, apparatus 100 may use a Wi-Fi connection to communicate with a smartphone app that accepts and processes (local or remote) user settings and conditions, such as exposure time, exposure intensity, spatial configuration, skin pigmentation, health condition, etc. Similarly, controller 104 may obtain inputs via a connection (e.g., an API) to a smart home system or the cloud. In instances where more than one apparatus 100 is installed in the same chamber or location, the wired or wireless communication interface may be used to synchronize timing, light intensity, dosages, or entire recipes and operation of apparatus 100 from a single user interface.

In embodiments, controller 104 may indicate the status of apparatus 100, e.g., by using an indicator light that signals an operation in a mode that generates UV light, thus, serving as a warning to users to not look directly at apparatus 101. Other indicators may signal the status of battery 107 and or other aspects of the operation of apparatus 100.

It is understood that controller 104 may communicate any type of information, such as exposure settings, use patterns, sensor information, and other information to any number of internal or external components and devices. It is further understood that controller 104 may manage the operation of the different light sources in any number of apparatuses, e.g., to enhance therapeutic and aesthetic benefits, while minimizing potentially harmful effects of light, such as skin or DNA and RNA damage. For example, in embodiments, controller 104 may manage UV-C exposure independently from visible, IR, or UV-B exposure in order to deliver the benefits of disinfection, sanitization, and mold-growth prevention, while avoiding light exposure to the human skin. In embodiments, controller 104 may use an internal clock circuit to cause apparatus 100 to deliver, for a relatively brief period of time, a defined dose of UV-C to sterilize nearby surfaces. On demand UV-C exposure may advantageously be used to rapidly and efficiently kill pathogens, such bacteria and viruses from on clothing and to-be-disinfected surfaces. For example, apparatus 100 may be used to decontaminate N95 respirators or protective clothing for multiple-user reuse to prevent exposure to airborne pathogens (e.g., SARS-CoV-2) that cause coronavirus diseases, such as Covid-19, and similar diseases. For added safety, controller 104 may use signals from any number of from sensors to prevent or disable UV-C exposure, in response to detecting the presence of a person near apparatus 100.

In embodiments, controller 104 may feed input data, e.g., from sensors, remote devices, the cloud, user input, etc., into a model to train the model to operate light source 101 to achieve desired results under varying conditions. To accomplish this, controller 104 may use various learning algorithms, e.g., deep learning techniques for neural networks, such as stochastic gradient descent and back propagation. A trained model may be used, for example, to use learned input data (observed data) from a set of sensors that detect and/or monitor skin tone, environmental conditions, and a user's vital signs to automatically adjust an intensity, duration, and distribution of light exposure for a particular user in a particular environment to match learned output data.

In embodiments, controller 104 may monitor, over time, any number of characteristics or parameters, such as the response of a user's skin to the light exposure, e.g., by using image sensor data and appropriate image processing techniques, e.g., to adjust a light recipe in response to measured or determined changes to reduce a deviation from a therapeutic, aesthetic, or other target condition. For example, controller 104 may control exposure to UV light to achieve a desired skin tone (tan) and, based on sensor data and other feedback, adjust the intensity, duration, and/or distribution of light exposure over time interval such as to maintain a desired level of pigmentation. In embodiments, controller 104 may use queues, such as Bluetooth identifiers or facial recognition data, to recognize a specific user and, in response, execute a customized light recipe for that user.

Although not shown in FIG. 1A, in embodiments, one or more sensors may be installed at strategic locations in a chamber to measure the amount of radiation at the location of a to-be-exposed object to allow controller 104 to do make real-time adjustments, e.g., via closed-loop feedback or other control methods. Similarly, inputs from other sensors—integrated or standalone—and data sources, such as a measured vitamin-D levels in the blood that, in embodiments, may be retrieved from an electronic health record may be used to adjust a light recipe to efficiently improve therapeutic, aesthetic, and other outcomes.

In embodiments, controlling dose, intensity, and exposure to certain wavelengths may comprise controller 104 managing safety interlocks (e.g., 105) to minimize the risk of potential harm, such as skin and eye damage that may otherwise result from prolonged UV exposure. In embodiments, since the reflectivity of nearby surfaces of the surroundings in which apparatus 100 is installed may impact the delivered amount of light generated by apparatus 100, controller 104 may adjusting the intensity of, e.g., UV-B light emission to low, medium, or high according to a configuration of the installation, i.e., by considering the distance of apparatus 100 to a user's body (skin and eyes) and the reflectivity of the walls in the exposure area. Similarly, controller 104 may use parameters, such as distance and reflectivity, to adjust the intensity of incident infrared light to prevent the light exposure from exceeding a threshold, e.g., 100 mW/cm$^2$, thus, preventing thermal ablation that may otherwise occur if optical power densities were to exceed about 200 mW/cm$^2$.

In embodiments, to protect against light overexposure, controller 104 may limit, e.g., the total UV exposure or dose (mJ/cm$^2$) for a user to a pre-defined period or time. As an example, in a bathroom setting comprising apparatus 100, UV-B exposure may be limited to the first 3 to 5 minutes a person spends in the shower. In embodiments, controller 104 may receive an enable signal, e.g., from user interface 106 or sensor 105 prior to controlling an intensity and time of UV-B light exposure of the skin, e.g., for the purpose of generating vitamin-D or treating a skin condition, such as psoriasis, vitiligo, or eczema. To further protect users from overexposure, controller 104 may comprise certain daily wavelength or dosage limits, e.g., cumulative UV-B and/or UV-A exposure limits defined by a total exposure time that apparatus 100 may actively generate, e.g., in increments of minutes per day. In embodiments, a safety feature may require a code or button sequence input prior to enabling certain modes of operation, for example, to prevent children from inadvertently activating certain light recipes or modes of operation.

In embodiments, apparatus 100 may use input signals from, e.g., a camera, to perform image recognition and, in response to detecting a face and/or eye, pause or halt certain modes of exposure to reduce or eliminate exposure risks. Controller 104 may comprise predetermined time-of-day settings that may define periods of time during which certain types of exposures are permitted, e.g., based on a programmable exposure protocol. It is understood that certain settings may be user-definable, while others may be enforced by safety interlocks 105 to prevent users from overriding safety-critical limits. It is further understood that any number of apparatus 100 may be installed in a same location, e.g., to increase irradiance, irradiance uniformity, create and manage different zones of light exposure, and control the exposure of the skin to the light.

User interface 106 may be implemented as a physical or virtual device. In physical embodiments involving manual operation, interface 106 may comprise an interface panel having buttons, switches, indicator lights, and/or a display that may be integrated into apparatus 100, e.g., to create and control light recipes. It is understood that user interface 106 may be implemented as a separate standalone device that may communicate (e.g., wirelessly) with apparatus 100 and that may be battery powered, self-powered, or powered by a line voltage.

Figure 10:
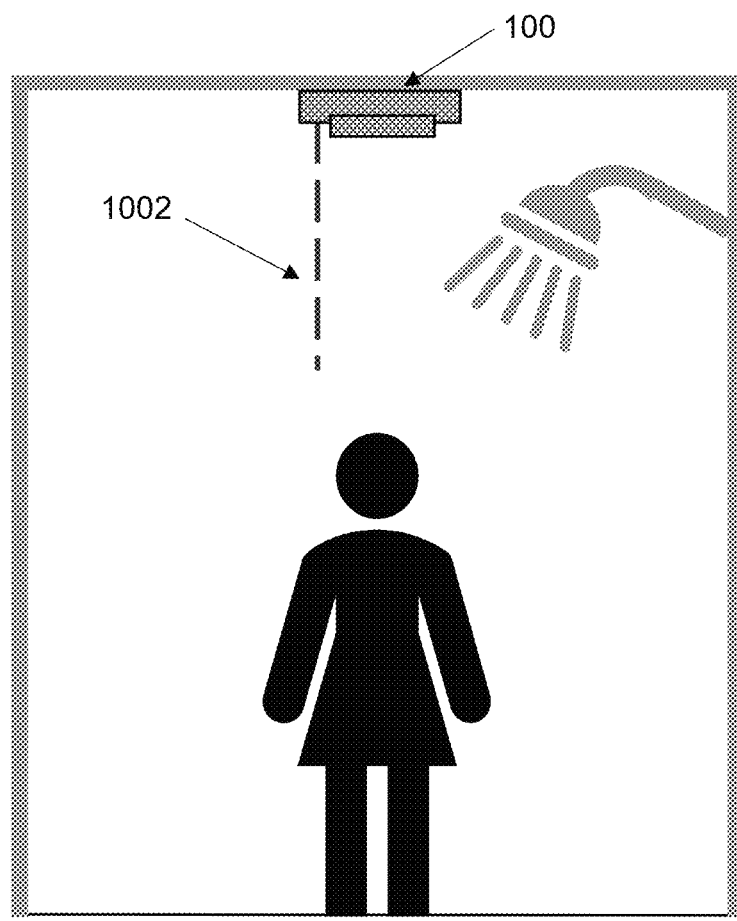
FIG. 10 illustrates an exemplary user interface interacting with a pull-chain according to various embodiments of the present disclosure.

In embodiments, user interface 106 may interact with pull-chain 1002, as shown in FIG. 10, e.g., to allow a user to initiate a light-exposure sequence. However, this is not intended as a limitation since, in embodiments, for example, a microphone (not shown) may be used receive audio input, such a voice command or the sound of water flowing in a shower, and, in response, initiate the light exposure sequence. In embodiments, a video camera may use image processing techniques to recognize a user's gestures to commence or halt a light exposure sequence. In addition, the camera input may be used to aid in implement safety interlocks, e.g., by automatically disabling any UV exposure after recognizing a human face or eyes. In virtual embodiments, a smartphone app or a smart-home software interface may be used, e.g., to wirelessly receive user input and other inputs comprising a desired dose, duration, geometry of an installation, skin-type, health condition, etc., to control apparatus 100.

In embodiments, any number of parameters that may be used to operate apparatus 100 may be automatically calculated, e.g., based on input from sensors 105, which may advantageously reduce the need for input via user interface 106. In embodiments, a machine learning or dedicated program may be used to convert input from sensors 105 into action, e.g., to automatically commence and control a light exposure sequence. For example a distance or proximity sensor may be used to measure a distance between apparatus 100 and a user to adjust the intensity of light emission to deliver a controlled dose of light to the user's skin. Similarly, a camera or spectrometer may be used to determine a user's skin type, e.g., by measuring skin reflectivity as a function of wavelength to assess both skin type (e.g., pigmentation) and skin condition (e.g., moisture content, sun damage, etc.). In embodiments, user-related and environmental information may be used to automatically adjust a light recipe, for example, to emphasize a healing over tanning. A look-up table may be used to correlate skin-type to recommended exposure of UV and IR light to aid in making appropriate adjustments. It is understood that any type of sensor and input may be utilized to monitor a skin condition over time, e.g., as a function of treatment.

Figure 1B:
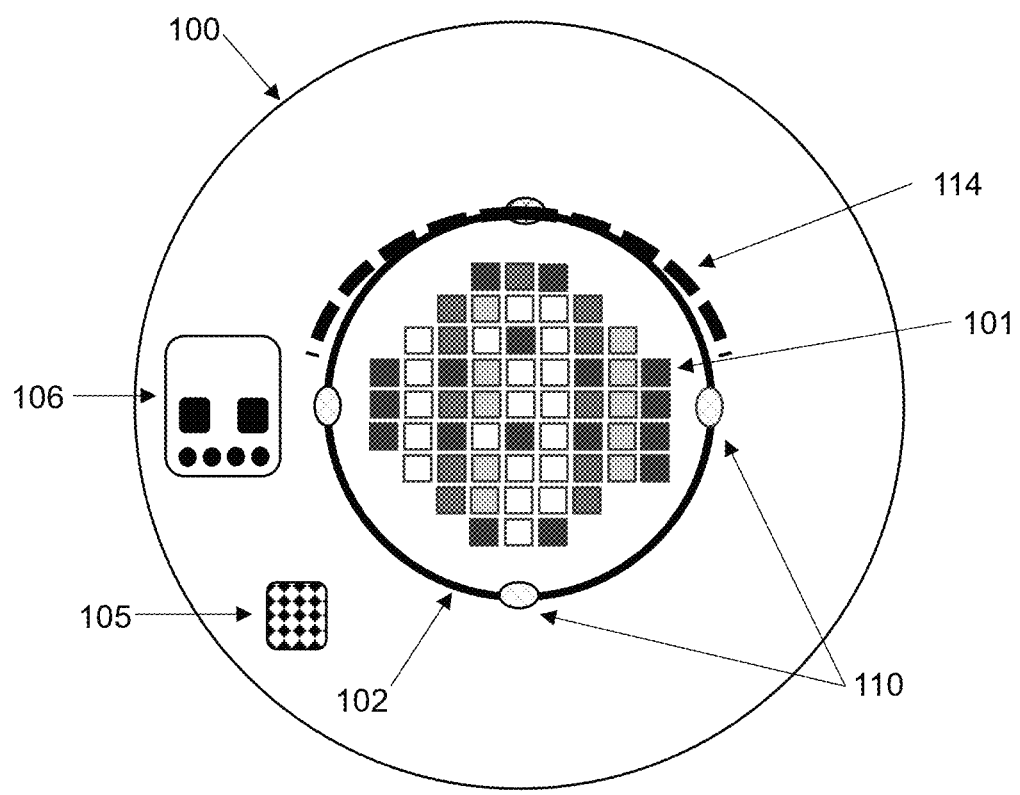
Figure 1C:
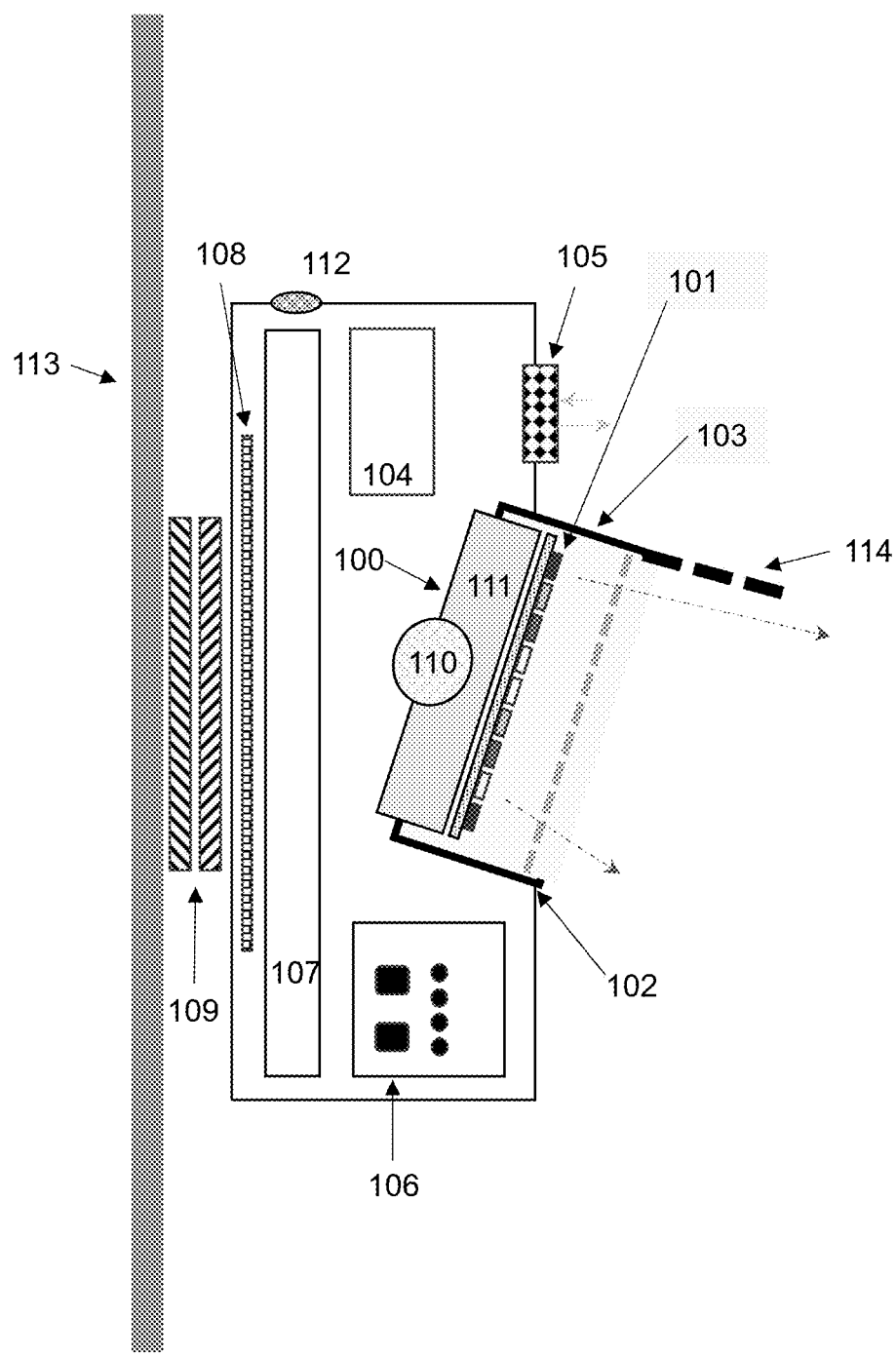

FIG. 1B is a plan-view of an exemplary modular light generation and delivery apparatus comprising a shutter according to various embodiments of the present disclosure. FIG. 1C is a side-view of the apparatus in FIG. 1C shown in a retrofit embodiment. As depicted, in FIG. 1C apparatus 100 comprises light source 101, optical cavity 102, diffuser 103, controller 104, sensor 105, user interface 106, battery 107, wireless charging coil 108, heat-sink 111, port 112, and optical shield or shutter 114. For clarity, components similar to those shown in FIG. 1A are labeled in the same manner. For purposes of brevity, a description or their function is not repeated here.

In embodiments apparatus 100 may comprise optical control elements 114, such as a shutter, which may be coupled to apparatus 100 by mechanical control elements, such as pivot point 110, gimbles, hinges, or other mechanisms to allow optical cavity 102 and light source 101 to be directed at certain directions, e.g., to spatially direct and/or focus light exposure.

It is understood that, in embodiments, optical cavity 102 may be water resistant or water proof, e.g., for applications in high-humidity environments, such as showers, saunas, and the like. In embodiments, apparatus 100 may comprise packaging that reduces or eliminates pathways for moisture penetration. It is understood that any number of electrical, mechanical, or optical components associated within apparatus 100 may be protected from potentially damaging moisture, e.g., by providing hermetic sealing, such as IP65, IP66, or IP67-rated sealings.

Figure 2A:
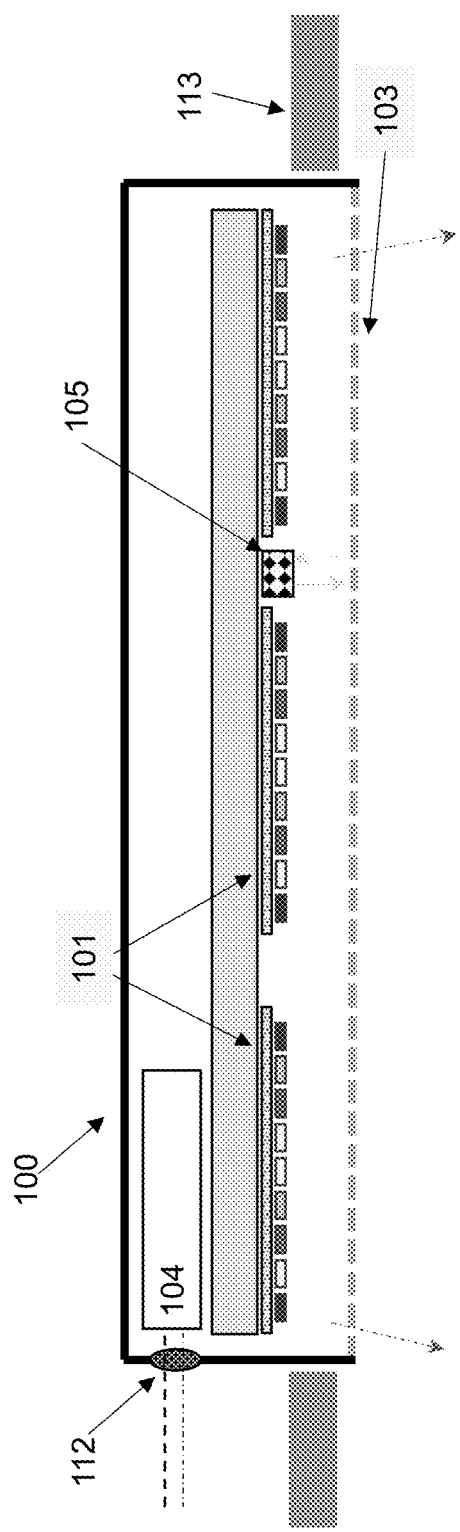
FIG. 2A is a side-view of an alternative light generation and delivery apparatus according to various embodiments of the present disclosure.
Figure 2B:
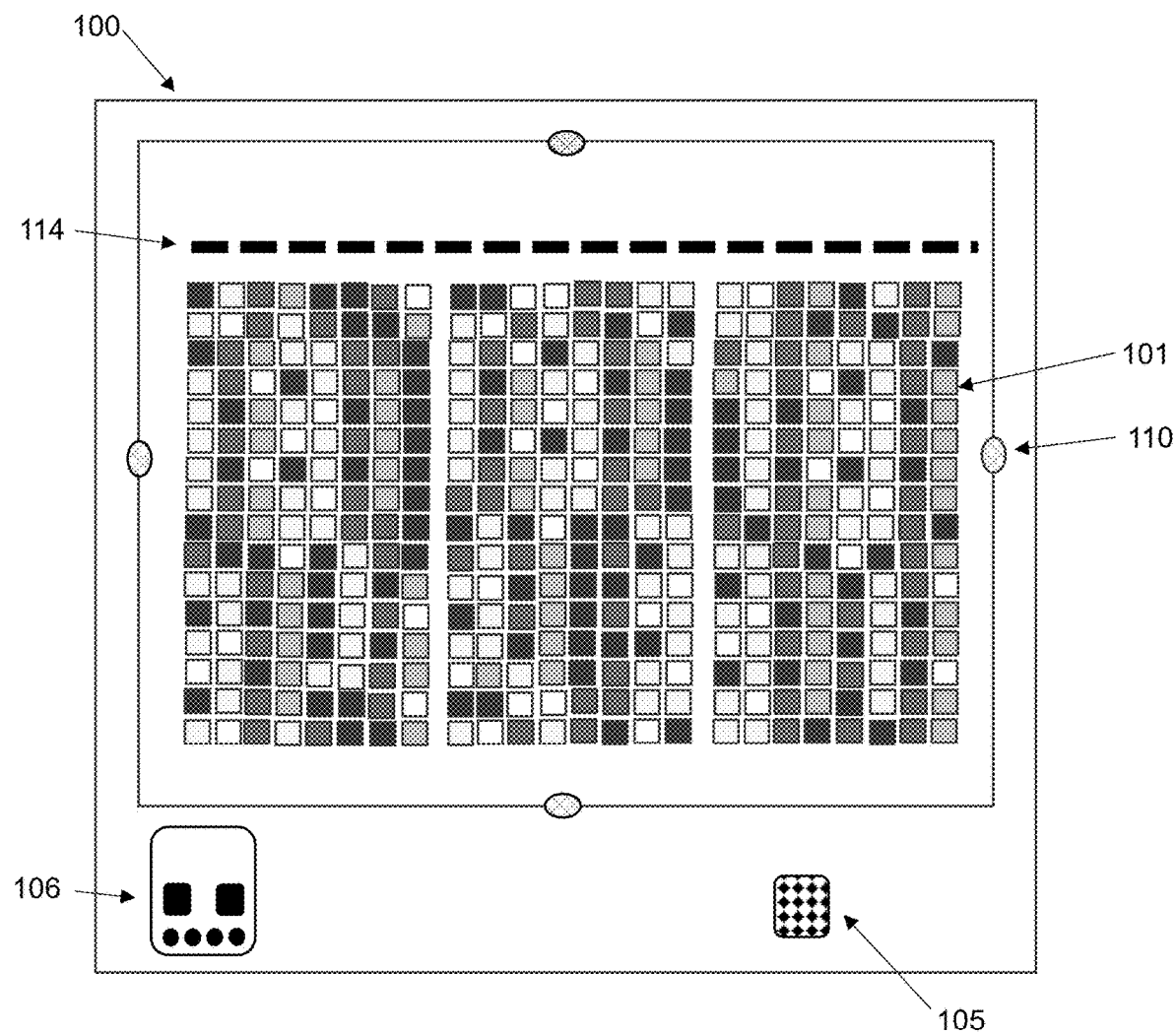
FIG. 2B is a plan-view of the apparatus shown in FIG. 2A.

FIG. 2A is a side-view of an alternative light generation and delivery apparatus according to various embodiments of the present disclosure. FIG. 2B is a plan-view of the apparatus shown in FIG. 2A. Unlike the apparatus shown in FIG. 1A, apparatus 100 in FIG. 2A is a "built-in" embodiment where one or more apparatus 100 may be ceiling-mounted or installed on a wall or fixture that supports the weight of apparatus 100.

In operation, apparatus 100 may be powered by a line voltage to generate and deliver a light for any length of time without interruption or maintenance. It is noted that apparatus 100 may comprise a back-up battery (not shown), e.g., to retain clock settings in the event of power loss. In a manner similar to FIG. 1A, apparatus 100 in FIG. 2A may be controlled, e.g., using an integrated or separate user interface, to control the emission of light from light source 101 having any of the previously mentioned characteristics, and thus a user's exposure to such light.

Figure 9:
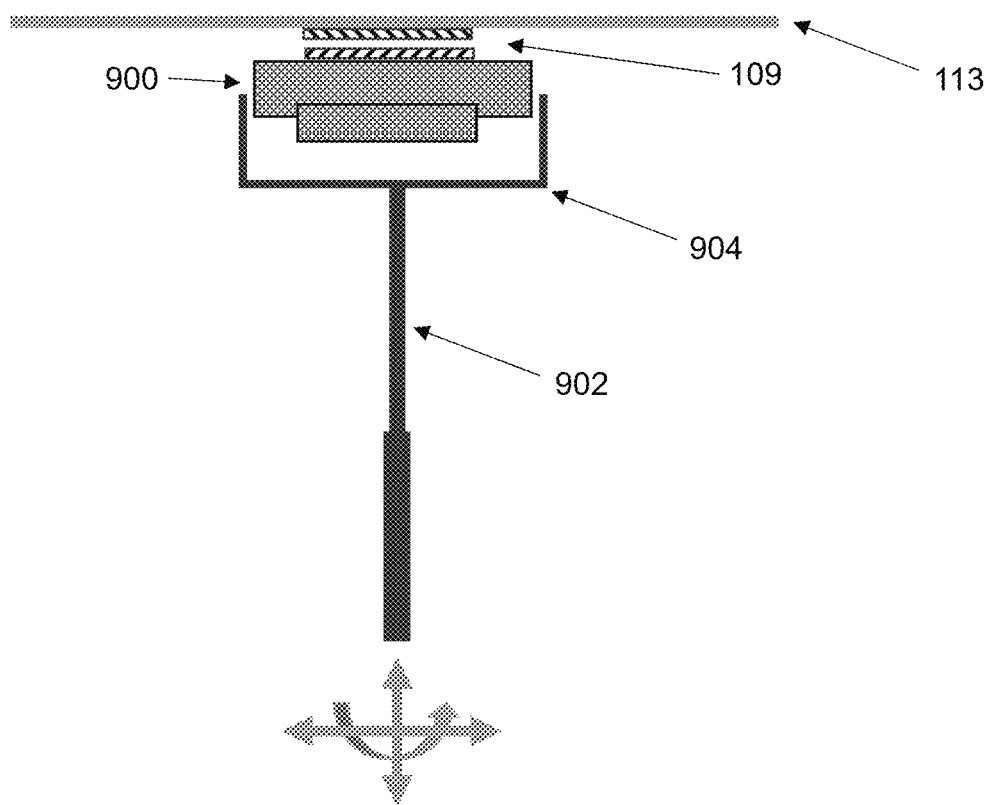
FIG. 9 illustrates an exemplary telescoping pole or claw according to various embodiments of the present disclosure.

As shown in FIG. 9, in embodiments, apparatus 900 may be designed to receive telescoping pole or claw 902 to allow users to reach, release, and reattach apparatus 900 from ceiling 113 without the need for a ladder or a stool. In embodiments, one end of telescoping pole 902 may comprise coupling 904, e.g., a twist-lock, clip, magnetic release, or other attachment that may mate with apparatus 900 to facilitate release and reattachment.

As previously mentioned with reference to FIG. 1A, the reflectivity of walls and other environmental factors of an installation, such as the distance between apparatus 100 and a target area, the size of the illumination chamber, etc., effect the amount and characteristics of light and, thus, dosages that apparatus 100 may deliver onto the target area.

In embodiments, the amount of light delivered by apparatus 100 and, thus, the delivery of specific therapeutic dosages and wavelengths of light and other benefits may advantageously be increased when surfaces near apparatus 100 comprise materials or coatings that have certain reflective properties in a range of wavelengths similar to that generated by apparatus 100. It is understood that controller 104 in apparatus 100 may be used to adjust any number of channels of light source 101 to tailor light in a manner that satisfies desired characteristics, such as wavelengths, dosage, etc. In addition, embodiments may take advantage of the physical geometry of the environment in which in apparatus 100 operates to enhance one or more target zones of illumination.

Figure 2C:
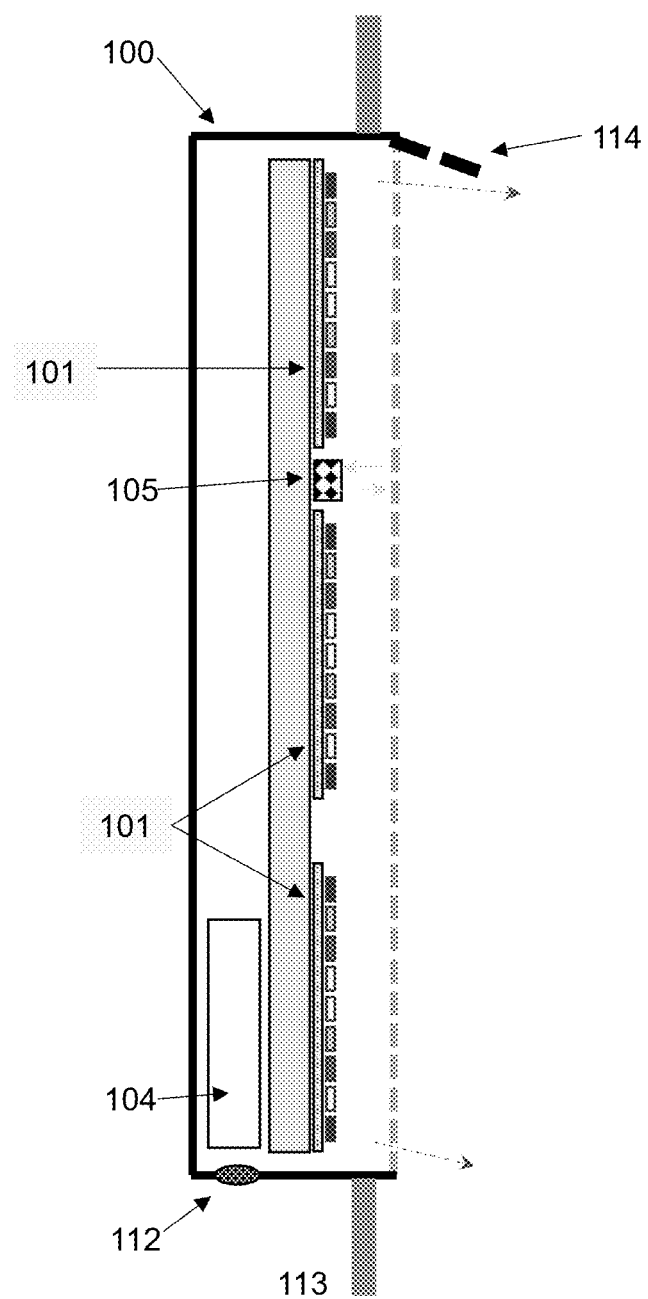
FIG. 2C is a side-view of an exemplary alternative light generation and delivery apparatus in FIG. 2A comprising a shutter according to various embodiments of the present disclosure.
Figure 2D:
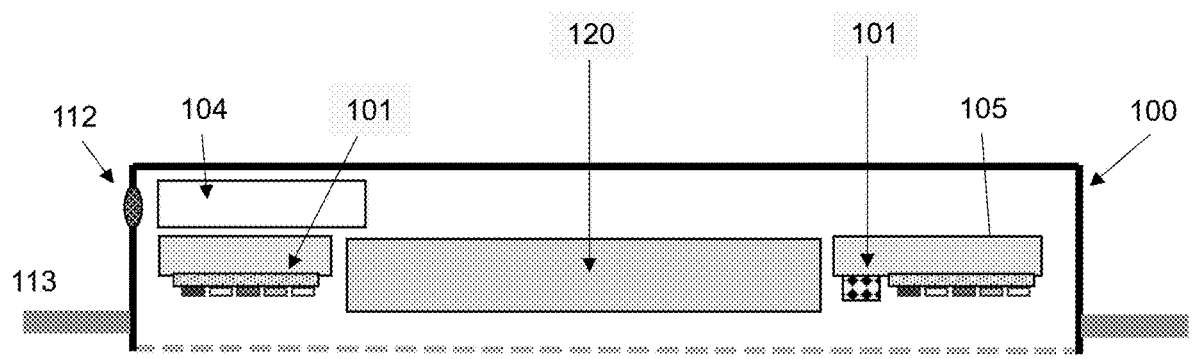
FIG. 2D is a side-view of an alternative light generation and delivery apparatus comprising a display according to various embodiments of the present disclosure.
Figure 2E:
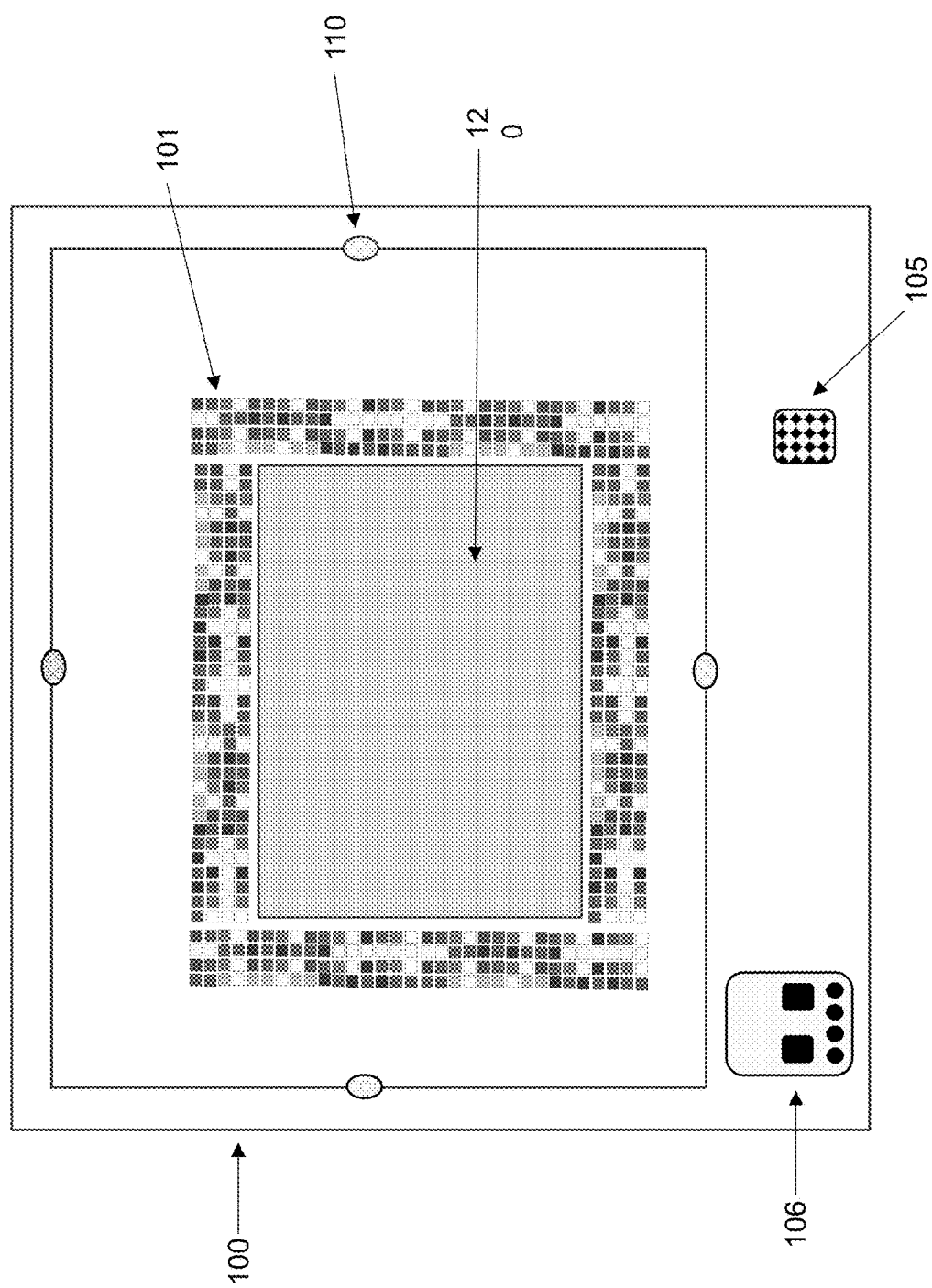
FIG. 2E is a plan-view of the apparatus shown in FIG. 2D.
Figure 2F:
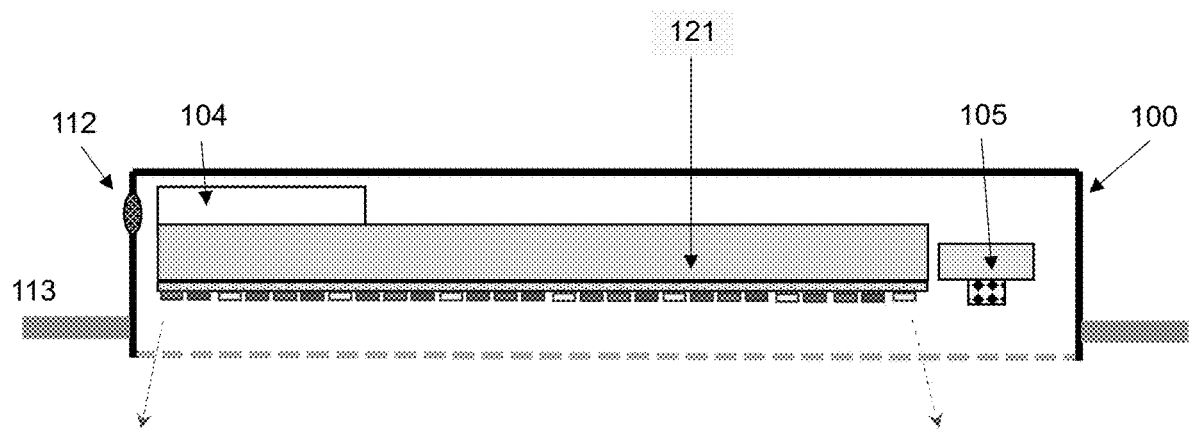
FIG. 2F is a side-view of an alternative light generation and delivery apparatus comprising an integrated display according to various embodiments of the present disclosure.
Figure 2G:
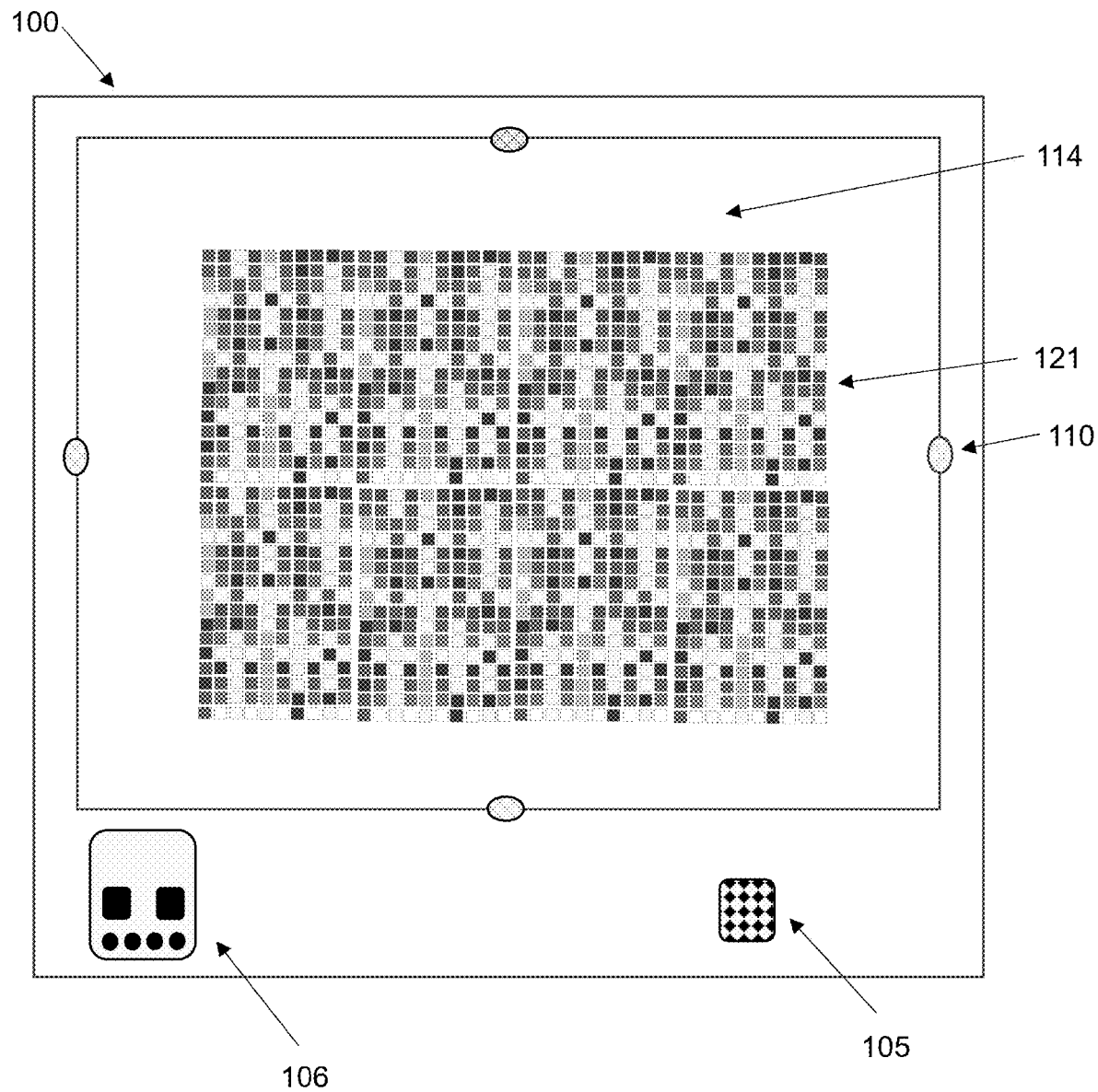
FIG. 2G is a plan-view of the apparatus shown in FIG. 2F.

FIG. 2A-2I illustrate various embodiments of a built-in apparatus. FIG. 2A and FIG. 2B illustrate assemblies that comprise individually controllable LEDs or other light sources, whereas FIG. 2C through FIG. 2I illustrate assemblies that integrate discrete light sources and display elements. In embodiments, the integration of display and display-like elements, such as micro-LED, liquid crystal (LCD) or organic light emitting diode (OLED) displays allows apparatus 100 to deliver images or video content, e.g., an image of the sky. This may be accomplished by using designated display 120 to deliver such content, and light sources 101 to deliver light at wavelengths and doses to facilitate therapeutic and aesthetic benefits as shown in FIG. 2C.

Figure 2H:
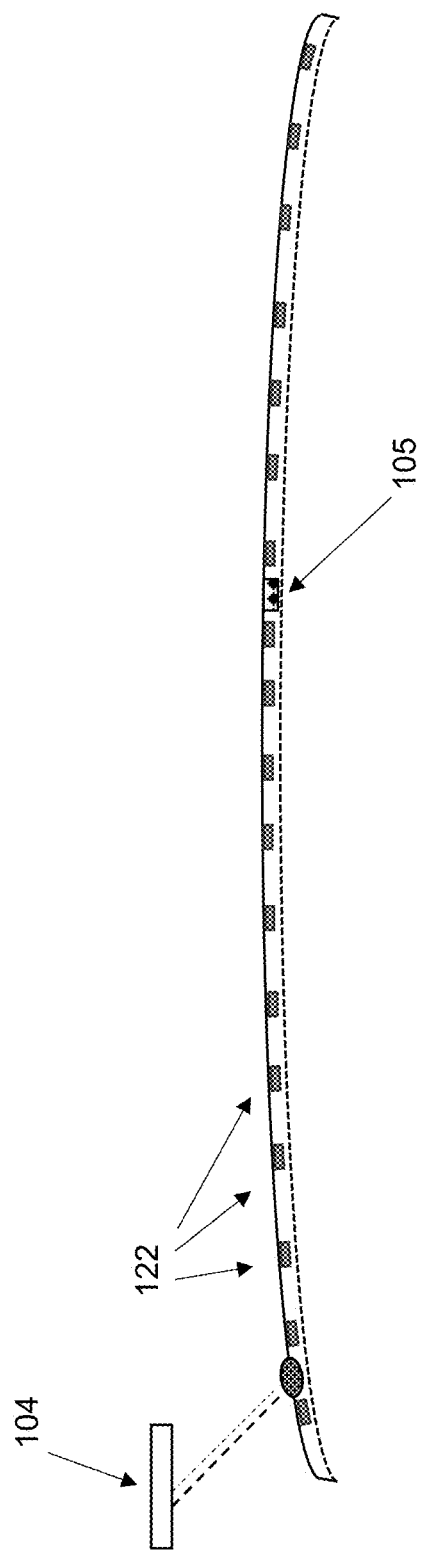
FIG. 2H is a side-view of an alternative light generation and delivery apparatus comprising locally integrated display elements according to various embodiments of the present disclosure.
Figure 21:
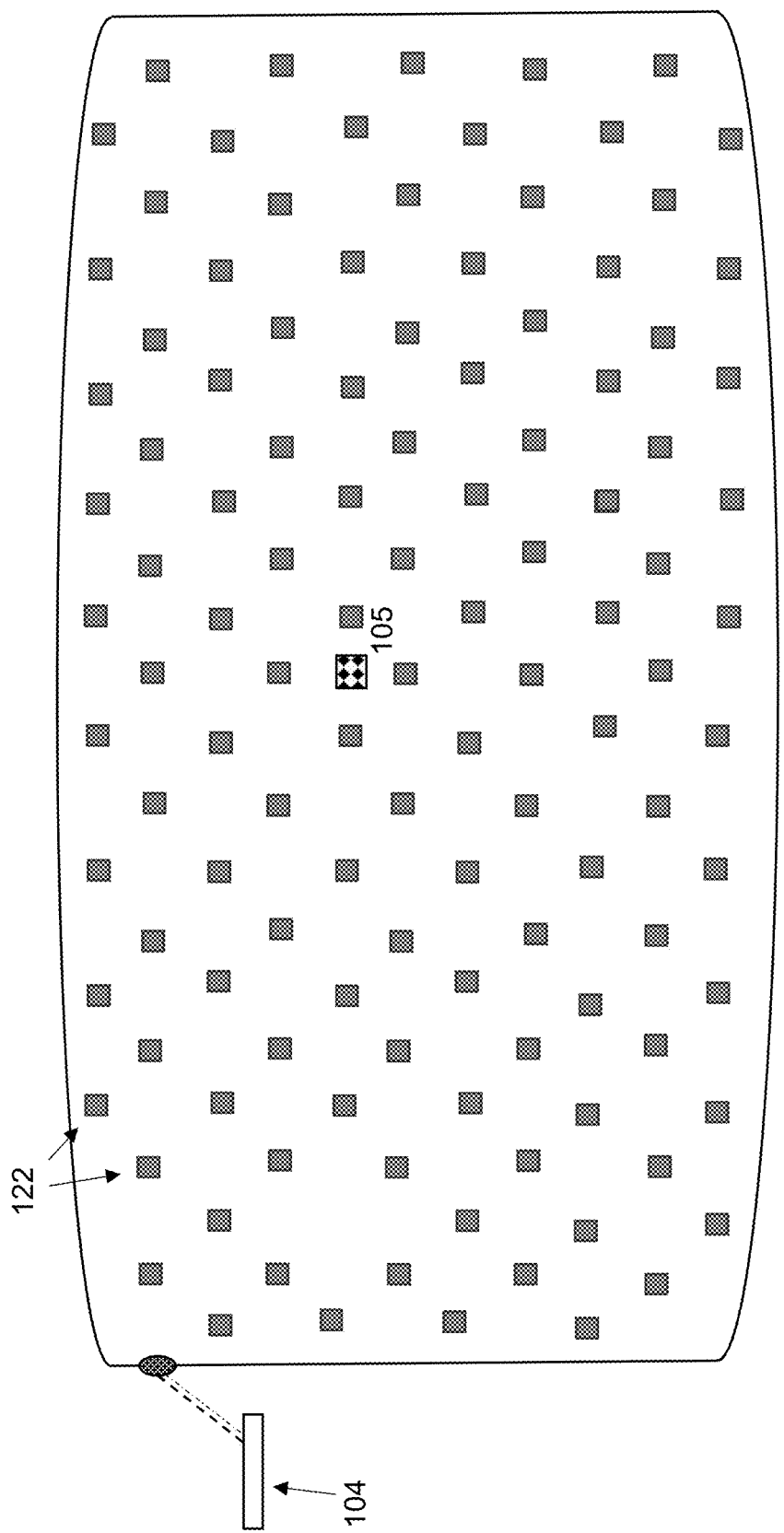

As shown in FIG. 2E through FIG. 2I, in embodiments, display elements and light sources may be integrated 121, 122 to deliver light having certain the wavelengths at certain doses. For example, the brightness and form-factor of micro-LED displays may enable the generation of visible light, e.g., for image formation, and light in the visible spectrum, infrared light, or invisible light (e.g., light having wavelengths in the UV-B, UV-A, and IR spectra) for use in therapeutic, aesthetics, and other applications. In embodiments, as shown in FIG. 2H, display elements 122 may be integrated into any type of substrate, e.g., to facilitate the creation of luminous surfaces. It is understood that such substrates may have any suitable geometry, e.g., a flexible curved surface.

In embodiments light source(s) 101 may emit light directly or indirectly onto optical cavity or mixing chamber 102. Optical cavity 102 may comprise diffuser 103 that may comprise or be made of a UV, IR, or optically transparent window material, e.g., quartz, or any other material suitable for optics components. In embodiments, optical cavity 102 may be used to focus or direct light emitted by light source 101, mix light emitted from different light sources, or reflect light to enhance light output of light source 101, e.g., to improve the uniformity of illumination or the appearance of apparatus 100, e.g., by disguising light source 101 and other mechanical or electronic components.

As illustrated in FIG. 3, in embodiments, reflectors 302, 304, lenses 306, 308, shields, shutters, or any combination of such optical components may be used to control of the flux from various light sources. In embodiments, the combination may utilize cut-off angles beyond which a light source cannot provide any substantial optical flux. Given that many light sources emit light over a broad range of angles, reflectors, lenses, shutters, and other optical components may be used to direct light onto certain regions, e.g., a target region of the human body. In embodiments, optical components may be used to create zones or regions of different illumination.

For example, as shown in FIG. 3A and FIG. 3B, parabolic reflectors 302, 304 may be used to concentrate light emission, e.g., from a Lambertian source, into a narrower range of angles, e.g., 10° to 90°. In embodiments, as shown in FIG. 3C and FIG. 3D, symmetric and/or asymmetrically shaped lenses may be used to create oblong or rectangular fields of light from less focused light sources. It is noted that lenses and reflectors may be used in combination to achieve a desired spatial light distribution.

Figure 3E:
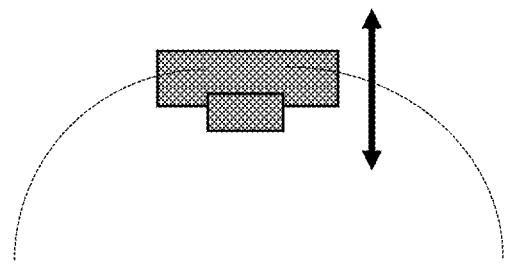
Figure 3F:
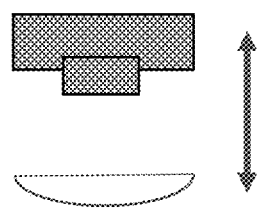

In embodiments, optical/focusing elements may be incorporated directly into light sources, or may be external or separate from light sources. For example, focusing elements, such as reflectors and lenses, may be built directly into the chip structure of LEDs or may be embedded into the packaging of the LEDs. In embodiments, the physical (or virtual) position of a light source may be adjusted relative to an optical element (reflector, lens, etc.), such that the focal-length of the optical element may be adjusted, as illustrated in FIG. 3E and FIG. 3F.

Figure 4:
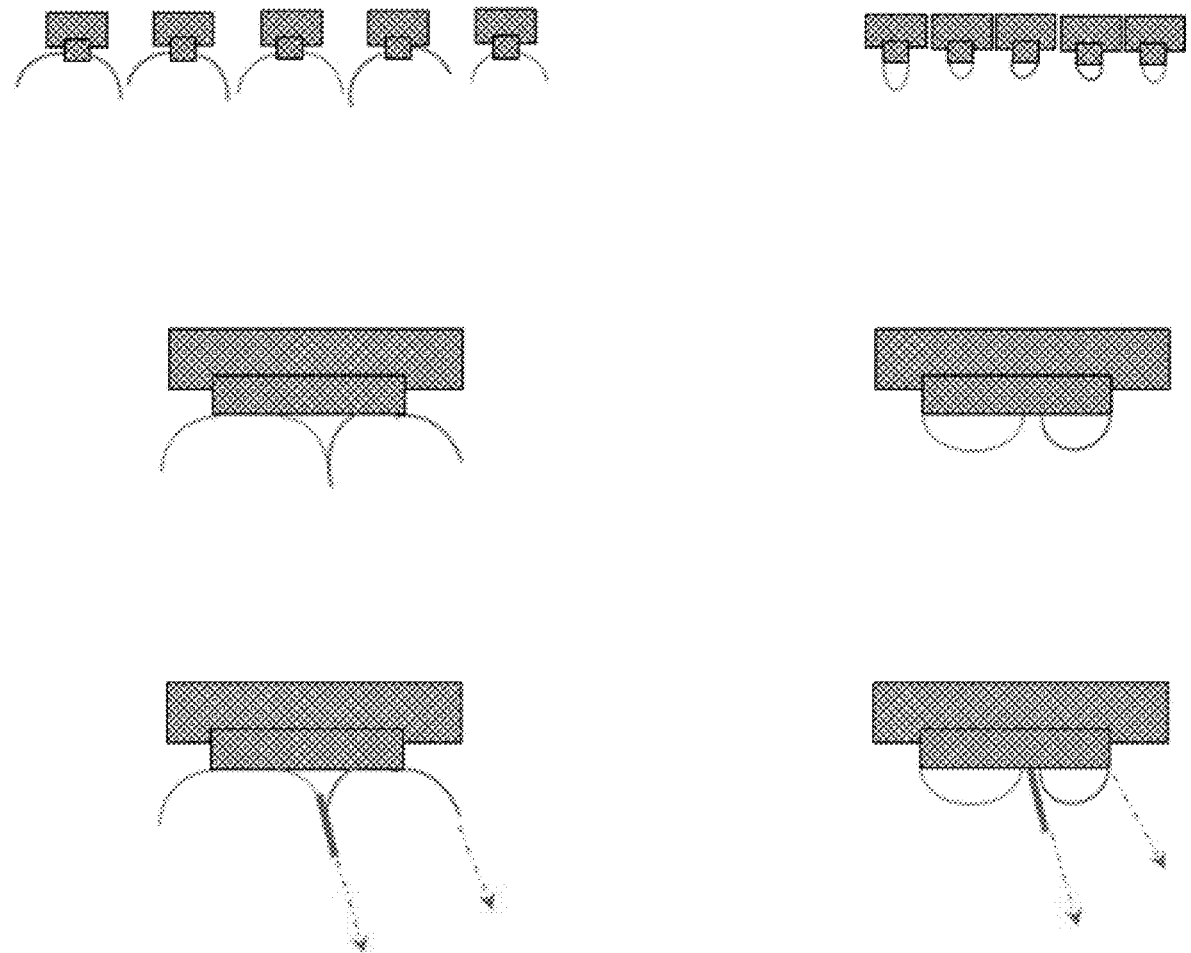
FIG. 4 illustrates segmented optical elements around light sources to generate zones of illumination according to various embodiments of the present disclosure.
Figure 6A:
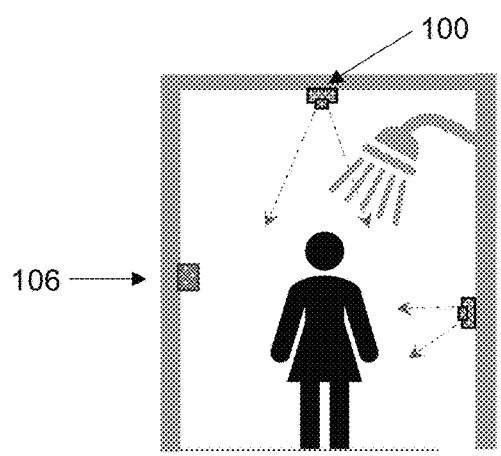
Figure 6B:
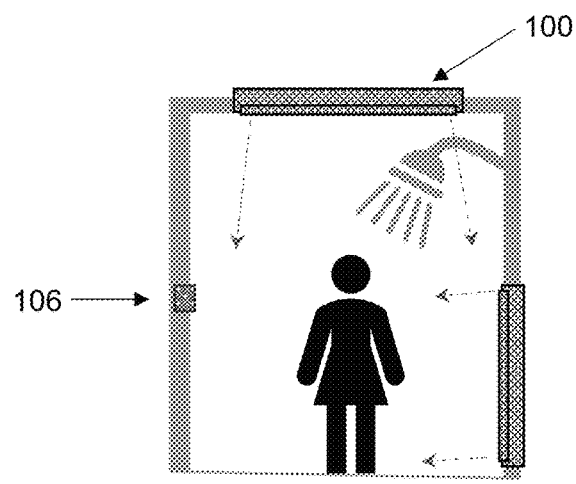
Figure 6C:
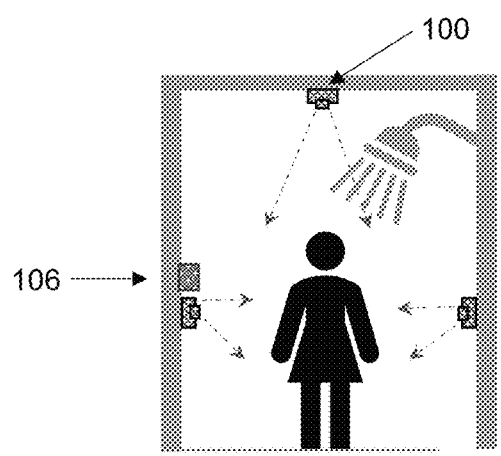
Figure 6D:
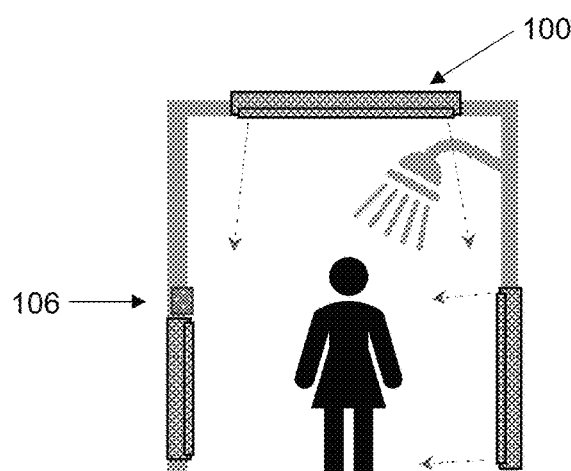

FIG. 4 illustrates segmented optical elements around light sources to generate zones of illumination according to various embodiments of the present disclosure. As depicted, optical elements such as lenses, reflectors (internal or external to a device), and shields (or shading/shutter devices), may be used to segregate light emission by wavelength range and/or light-source type in order to deliver different wavelengths to different zones of illumination and/or to block light from reaching certain angles and, thus, e.g., certain body parts. As mentioned with reference to FIG. 1C, in embodiments, one or more optical cavities may be mechanically distinct from apparatus 100 and may be attached to apparatus 100 using pivots, gimbles, hinges, or other mechanisms that may allow an optical cavity and the light source to be "pointed" in particular directions to physically direct and/or focus light exposure. For example, an apparatus may be configured to deliver visible or infrared light to a broad area (e.g., an entire body), while UV light may be delivered, e.g., to a relatively narrower region (e.g., below the neck). In embodiments, for example where the apparatus is placed on a wall, an optical shield may be used to define one exposure region that comprises a human body but avoids or minimizes exposure to the human face. In embodiments, optical control features of the apparatus may be used to increase or focus a delivered dose of light to a certain area and define the exposure region for various light sources.

As shown in FIGS. 5A-5D, FIGS. 6A-6D, and FIGS. 7A-7D, apparatus 100 may be configured in any number of ways. FIG. 5A, FIG. 5C, FIG. 6A, and FIG. 6C illustrate a retrofit embodiment in which apparatus 100 may be attached to the ceiling or wall of a chamber, such as a shower, sauna, pool or any space in which typically a significant fraction of a person's skin is exposed. Such retrofit embodiments may operate without requiring a significant wall-penetration or a wired connection. Instead, apparatus 100 may be battery powered and removably affixed to a wall or ceiling to enable a quick release and reattachment for periodic recharging. Various embodiments may comprise an integrated user interface, e.g., for activating apparatus 100, and/or separate user interface 106 that may be attached (without penetration) to a wall or surface within reach of the user.

FIG. 5B, FIG. 5D, FIG. 6B, and FIG. 6D illustrate a built-in embodiment in which apparatus 100 may be integrated into a ceiling or wall and powered by line-voltage (wires). In such configuration apparatus 100 may comprise integrated and/or a separate user interface 106 that may be either attached (without penetration) or built-in.

Figure 7A:
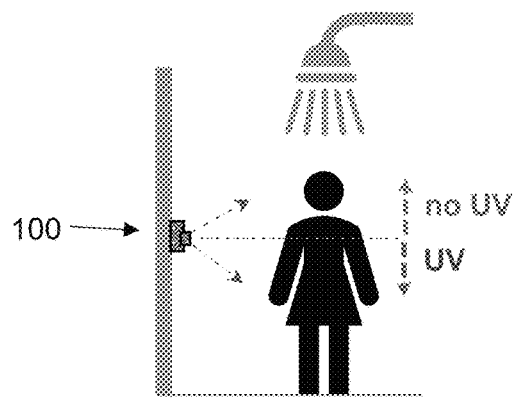
FIG. 7A-FIG. 7D, are side-views illustrating an exemplary light generation and delivery to different zones of illumination, according to various embodiments of the present disclosure.
Figure 7B:
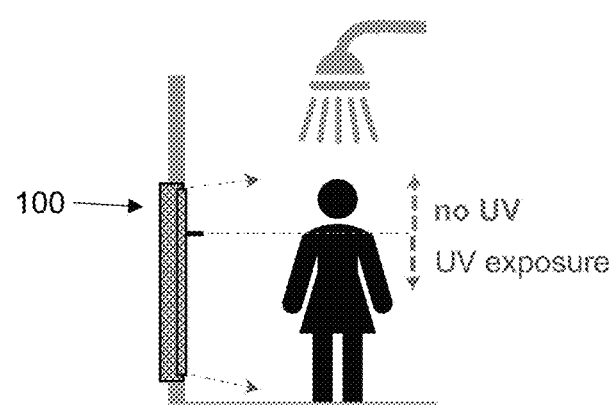

FIG. 7A-FIG. 7D, are side-views illustrating an exemplary light generation apparatus configured to deliver light to different zones of illumination, according to various embodiments of the present disclosure. As depicted in FIG. 7A and FIG. 7B apparatus 100 may accomplish this by using different optical segments (described previously). For example, optical shields, lenses, reflectors, or any combination thereof may be used to direct/limit the exposure of certain wavelengths of light to a user's body, e.g., below the user's neck, such as to prevent light exposure of the face and eyes. In embodiments, optical and electrical configurations of apparatus 100 may allow for certain zones to be defined differently for different wavelengths. For example, exposure to visible and infrared light may be permitted for the entire body, while UV light may be restricted to body parts below the neck to avoid light exposure of the face and eyes. Various zones may be enforced mechanically, e.g., by using a shutter or shield, electrically, or optically, and may be configured, e.g., at time of installation, or made user-configurable.

Figure 7C:
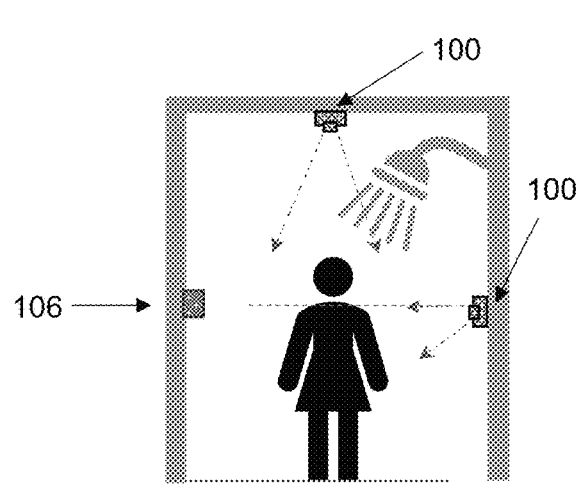
Figure 7D:
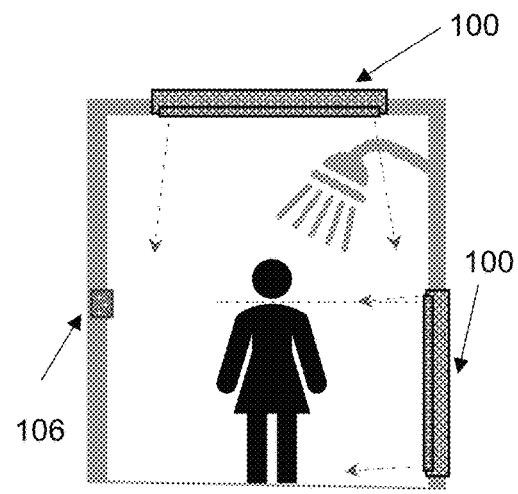

In embodiments, such as illustrated in FIG. 7C and FIG. 7D, any number of apparatus 100 may be used to illuminate any number of different zones. For example, apparatus 100 may be used to deliver certain wavelengths mounted overhead, while deliver a different set of wavelengths and intensities when apparatus 100 is wall-mounted. It is noted that the uses of apparatus in these illustrations are not limited to the constructions shown therein or described in the accompanying text. As a person skilled in the relevant art will appreciate, any combination of these configurations may be deployed. For example, visible and UV-C light may be delivered from apparatus 100 mounted on a ceiling, while UV-A, UV-B, and IR light may be delivered from a wall-mounted apparatus 100.

Figure 8A:
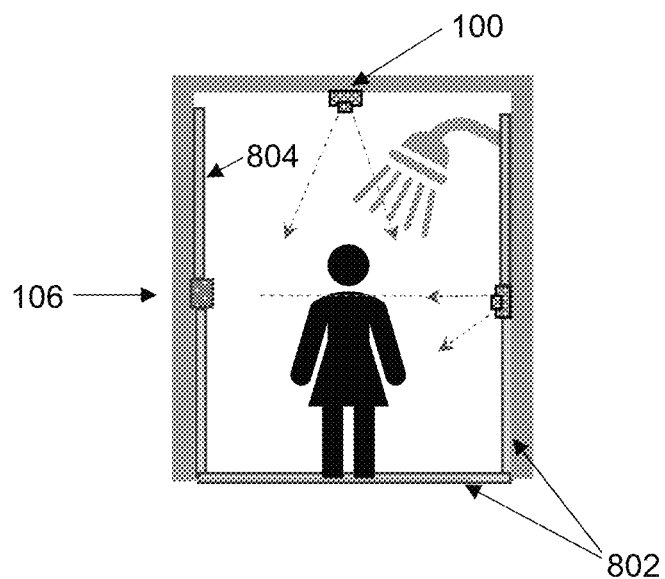
FIG. 8A and FIG. 8B illustrate exemplary uses of surfaces having different reflective properties according to various embodiments of the present disclosure.
Figure 8B:
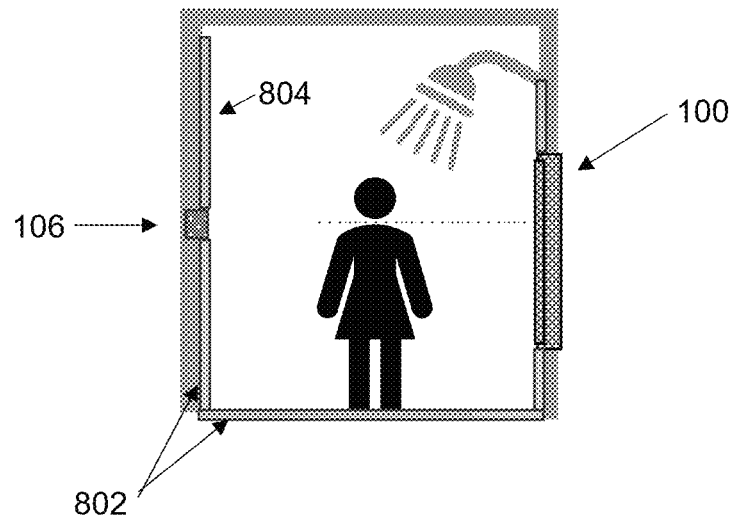

FIG. 8A and FIG. 8B illustrate exemplary uses of surfaces having different reflective properties according to various embodiments of the present disclosure. As depicted, lower portion 802 and upper portion 804 or a shower surface may have different reflective properties for a given wavelength(s). For example, lower portion 802 may be coated with or comprise UV reflective material, such as high reflectivity paint, or comprise aluminum or white tile, whereas the surface in upper portion 804, e.g., above chest height, may be coated with or comprise materials that absorb UV light, such as low reflectivity paint, glass, or concrete, and the like. Advantageously, such configurations may increase the amount of UV-B light delivered to a user's skin and body, while reducing the amount of UV-B light incident on the user's face and eyes. In other words, surfaces 802 and 804 create several zones of illumination that allow apparatus 100 to better control the delivery of light, thereby, improving the overall efficiency of light delivery.

In embodiments, coatings such as sintered polytetrafluoroethylene sheets may be used to provide relatively high visible, infrared and UV light reflectivity. In embodiments, materials may be chosen to selectively reflect certain wavelengths, while absorbing others. For example, one portion of a chamber wall may be comprise exposed aluminum to reflect a wide range of wavelengths, and another portion of the chamber wall may comprise aluminum backed glass (e.g., a mirror) to reflect light in the visible spectrum but absorb infrared and UV light. For example, glass may absorb the UV light, while the mirror may reflect visible light.

It is understood that properties of paints and other coating materials may be chosen based on reflectivity to similarly enhance or reduce the reflectivity. In this way, materials, coatings and/or paints may be used to enhance and control the illumination delivered to the skin and body.

Figure 11:
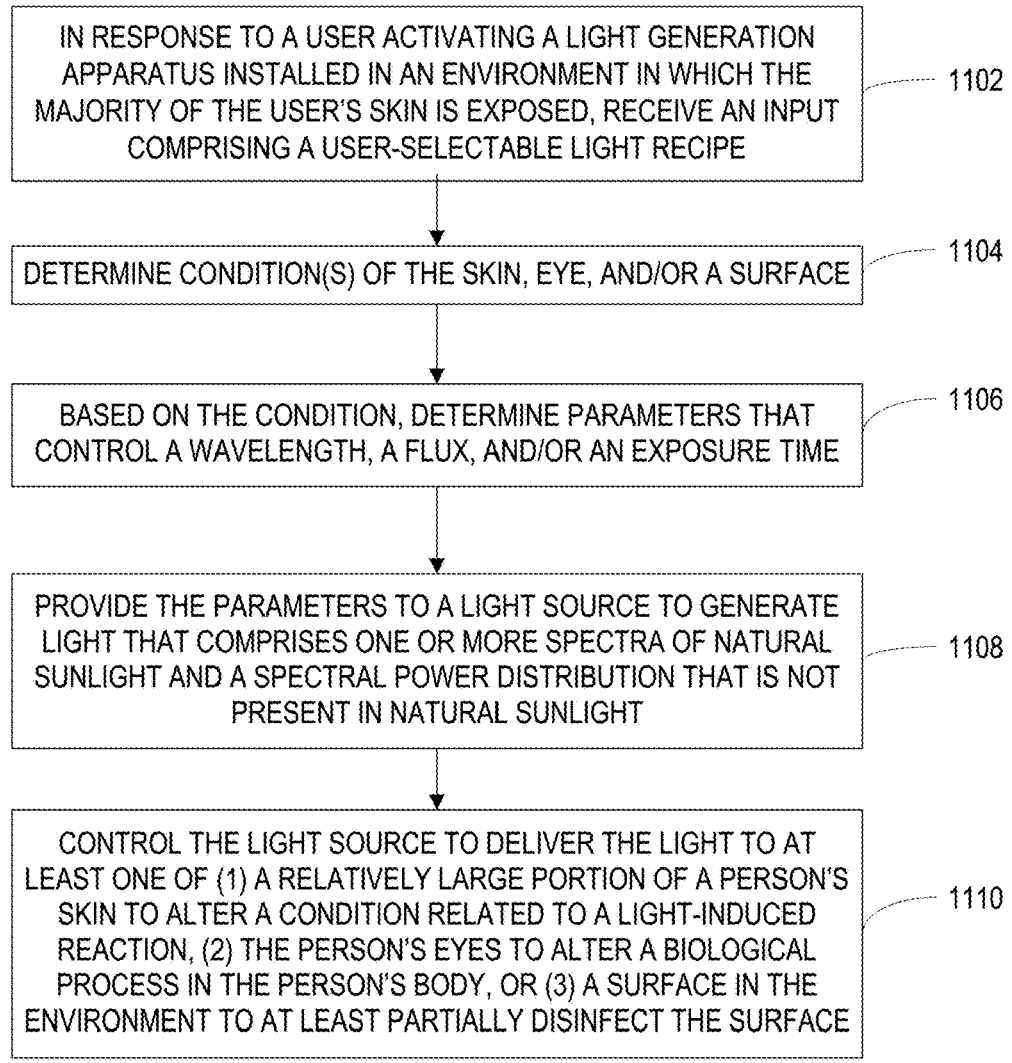
FIG. 11 is a flowchart of an illustrative process for operating a light generation and delivery apparatus in accordance with various embodiments of the present disclosure.

FIG. 11 is a flowchart of an illustrative process for operating a light generation and delivery apparatus in accordance with various embodiments of the present disclosure. In embodiments, process 1100 for light generation and delivery may start at step 1102 when a user selection is received, e.g., in response to a user manually or automatically activating a light generation apparatus. The apparatus may be installed in any environment, such as a shower, in which at least for a period of time the majority of the person's skin is exposed.

At step 1104, based on the user selection and a condition(s) of skin, eye, and/or surface, a set of parameters is determined that controls at least one of a wavelength, a flux, and/or an exposure time, e.g., via an embedded controller that checks safety interlocks (e.g., an occupancy sensor) and activates status and/or warning indicators (e.g., visual, acoustic, etc.).

At step 1106, based on the determination, the set of parameters may be provided to a light source to generate in one or more phases, according to a light recipe and in accordance with the condition(s), light that comprises one or more spectra of natural sunlight, a spectral power distribution not present in natural sunlight, or some combination thereof. In embodiments, a light recipe sequence may by initiated, e.g., as by a user pushing a button, pulling a chain, issuing a verbal command, making a gesture, or automatically using a motion or other sensor input that causes the controller to execute the light recipe. Once a light sequence is initiated, the controller may check a number of inputs, such as user input (user ID, recipe type, etc.), sensor inputs, status of the apparatus (battery, emitter, etc.), time-of-day, and prior usage patterns to ensure safe operation and make automatic adjustments to the light recipe.

Once checks and adjustments to dose and intensity are complete, the controller may, at step 1108, begin the prescribed therapeutic and aesthetic light exposure by controlling the light source to deliver the light to at least one of (1) a relatively large portion of a person's skin to alter a condition related to light-induced reaction involving one or more layers of the person's skin, (2) the person's eyes to alter a biological process in the person's body, e.g., to alter a circadian rhythm, or (3) a surface in the environment to at least partially disinfect the surface.

It is noted that one skilled in the art will recognize that herein (1) certain steps may optionally be performed; (2) steps may not be limited to the specific order set forth herein; (3) certain steps may be performed in different orders; and (4) certain steps may be done concurrently.

A light recipe may be designed, e.g., to deliver an adequate dose of UV-B light to synthesize the users' daily dose of vitamin-D (e.g., 100 IU to 1500 IU), provide IR light to improve a skin condition, and deliver a strong dose of visible light as a circadian stimulus. An exemplary recipe may comprise several minutes of UV-B exposure to stimulate vitamin-D synthesis at low, medium, or high levels depending on skin type and configuration (e.g., distance, reflectivity of bath room walls) as determined or measured by any number of sensors, such as cameras, proximity sensors, etc. A recipe may further comprise a time-of-day setting appropriate for visible light for the duration of the shower to affect the circadian stimulus.

The intensity and duration of light exposure may be dictated by the light recipe that, e.g., stipulates light exposure for a pre-determined length of time, and/or responding to user input (e.g., a stop signal), and/or responding to sensor input, such as stopping after detecting prolonged inactivity or based on input from a safety interlock.

A recipe may further comprise a sterilization setting that activates UV-C light, e.g., to kill bacteria, viruses, and fungi from bathroom surfaces, e.g., to inhibit mold growth or disinfect the users' clothes once no user is present. In embodiments, e.g., once a shower cycle is completed time and/or sensor input may be used determine that to the shower is unoccupied prior to activating a light recipe that stipulates the delivery of UV-C light. In embodiments, if a light recipe calls for UV light exposure the apparatus and/or user interface may signal the presence of UV light, e.g., by activating an indicator light, audible tone, or display a warning sign, such that the user would know not to look at the light source.

Various embodiments increase the efficiency of light-activated therapeutic pathways in the human skin and body. Studies show the human skin is more efficient at vitamin-D synthesis at low doses of UV-B radiation (less than 10 mJ/cm$^2$) than at high doses (10+mJ/cm$^2$). The efficiency of vitamin-D synthesis is tied to the availability of pre-cursors in the skin, reaction kinetics, and other properties (e.g., pigmentation) that mostly favor higher efficiency at lower doses. Studies further suggest that vitamin-D synthesis is a self-limiting process, which from an evolutionary perspective is a natural defense against vitamin-D toxicity. Therefore, in embodiments, apparatus 100 may generate and deliver relatively modest doses of UV-B radiation (e.g., less than 10 mJ/cm$^2$) in a controlled manner to the human skin/body in environments where the majority of the skin is exposed. Causing the skin to absorb light over a larger skin area, advantageously, allows for a reduced overall dose per skin area to be administered to a person without sacrificing desired benefits, such as vitamin-D synthesis. Advantageously, such embodiments stimulate therapeutic pathways while lowering adverse effects of, e.g., UV-light that are tied to high dosage per skin area, such as sunburn, and skin aging, while, at the same time, increasing efficiency.

Systems and methods described herein deliver benefits at lower doses per-session than natural sunlight and faster than sunlight. For example, to obtain an adequate amount of vitamin-D from summer sunlight when only 15% to 20% of human skin is exposed (face, hands, and arms) requires about 30 minutes of exposure to noon-time sun light. In contrast, when fully exposed (sunbathing) this time drops to 5-10 minutes. The UV spectrum of natural sunlight is not efficient for vitamin-D synthesis, as it delivers >100× more UV-A flux than UV-B flux used for pre-vitamin-D synthesis. Embodiments that deliver UV-B for pre-vitamin-D synthesis, advantageously, substantially avoid the unnecessary UV-A exposure. As a result, embodiments enable users to synthesize healthy vitamin-D levels from a cumulative UV dose of less than 10 mJ/cm$^2$ per day as compared to two to three sessions of natural sunlight each week exposure skin to more than 500 mJ/cm$^2$ of UV radiation in each session.

In addition, the ability to deliver light in a comfortable setting in which much of a person's skin is invariably exposed greatly improves compliance, which is a critical determinant of therapeutic outcomes. Embodiments enable the integration of healthy light exposure into an existing daily routine, such as a daily shower routine. The ability to deliver therapeutic benefits without requiring medical intervention or a significant change in behaviors or habits, may, therefore, greatly improve desired outcomes. For example, apparatus 100 deployed in a shower in a retirement home may be programmed to automatically deliver UV-B exposure for vitamin-D generation without requiring any intervention or additional equipment. Given that elderly populations are at higher risk for vitamin-D deficiency and associated adverse health outcomes, the presented system and methods may provide meaningful improvements to users' health.

In embodiments, a controlled dose of light may be delivered according to a light recipe or a light sequence where particular wavelengths of light with specific intensities and durations are specified and/or adjusted to deliver the intended benefits. Light recipes may take many forms depending upon factors, such as the configuration of the apparatus, the benefits desired by the user, and changes in a users' needs or health condition. Light recipes may also be customized to the individual user, the time of day, time of year, location, and in response to sensor and/or other inputs. For example, a light recipe focused on vitamin-D synthesis may stipulate that an apparatus deliver UV-B light in the range of 0.01-10× the optical power of natural sunlight for 3 to 5 minutes. In another example, a light recipe focused on skin health may stipulate that the apparatus deliver IR light in the range of 0.1-10× that of natural sunlight. In yet another example, a light recipe focused on circadian health may stipulate that the apparatus deliver an time-of-day appropriate dose of visible light with an intensity of 1,000 lux to 20,000 lux. Finally, a light recipe focused on sterilization may provide periodic doses of UV-C light to disinfect and sanitize surfaces as well as inhibit the growth of mold.

It is noted that light exposures may occur concurrently or sequentially and may be provided in any combination of dose and intensity in accordance with the desired therapeutic and aesthetic benefits. The start and end of a light recipe may be triggered by a user (manually or automatically), sensors, or according to the time-of-day and may be ended, e.g., according to a defined time of exposure, through the user (manually or automatically), or in response to sensor input. Light recipes may be adjusted automatically, e.g., based on user input, sensor input, or external inputs, either in real-time, a priori, or after the fact.

Figure 12:
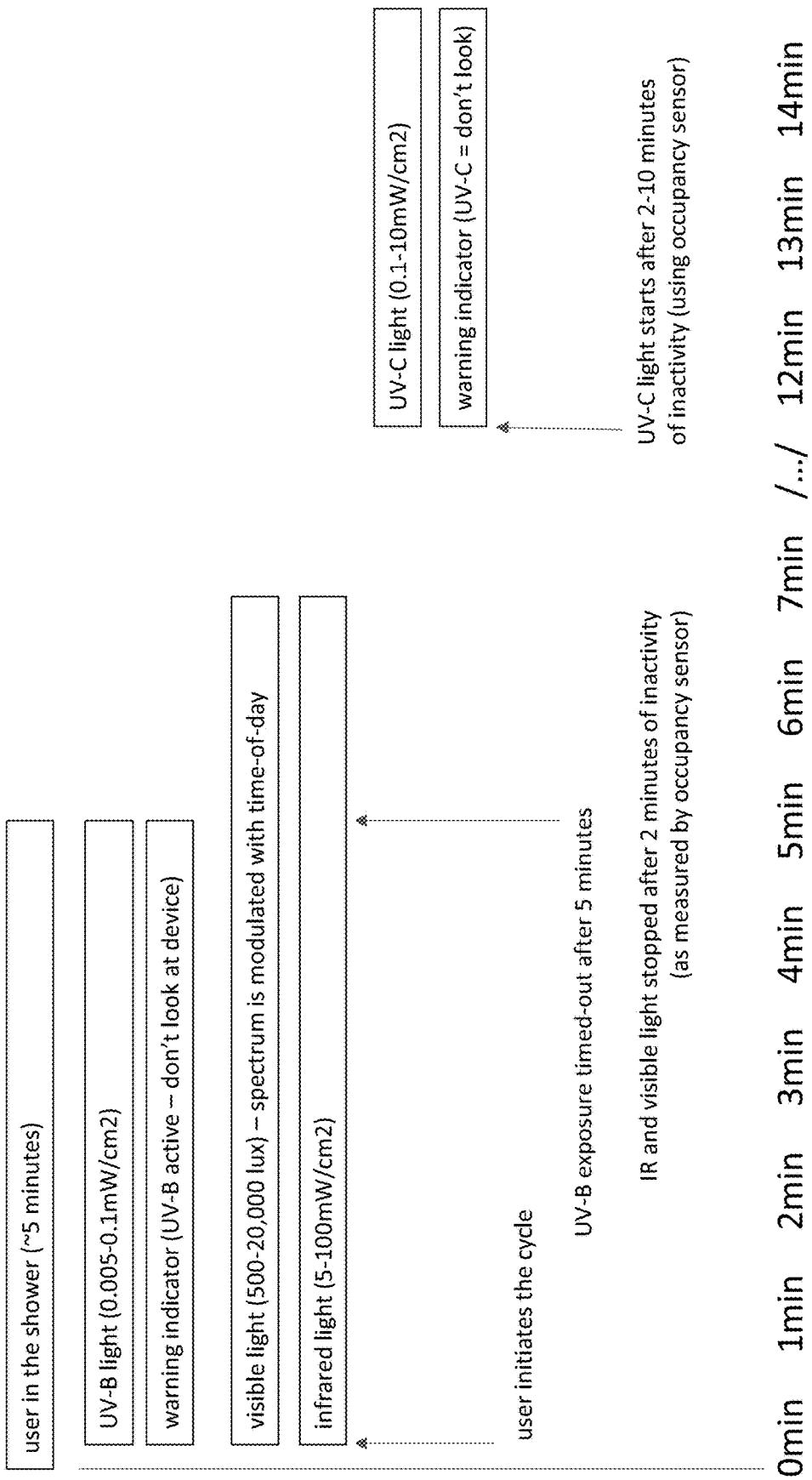
FIG. 12 illustrates an exemplary time-sequence operation of a light generation and delivery apparatus according to various embodiments of the present disclosure.

FIG. 12 illustrates an exemplary time-sequence operation of a light generation and delivery apparatus according to various embodiments of the present disclosure. Time-sequence 1200 operation may be used, e.g., by an apparatus placed in a shower to achieve benefits comprising UV-B exposure for Vitamin-D synthesis, IR light exposure for skin rejuvenation, and visible light for circadian stimulus. A user may initiate sequence 1200 (manually or automatically), after which the apparatus may deliver a controlled exposure of light according to the selected light recipe. As shown in example in FIG. 12, an apparatus may provide exposure to UV-B light for a defined time, here, about 5 minutes. The light intensity (mW/cm$^2$ of optical power) and total dose (mJ/cm$^2$) may be adjusted, e.g., according to factors such as a desired Vitamin-D synthesis, skin-type, skin-pigmentation, skin-condition, and other exposure preferences. In embodiments, adjustments may be made with an a priori user input and/or in real-time using sensor input data, e.g., in combination with a process, a look-up-table, etc., to optimize exposure conditions and durations.

For example, an apparatus may deliver 0.01 mW/cm$^2$ of UV-B light (e.g., 295 nm to 300 nm) to 80% of the skin (excluding the face) for 5 minutes to deliver a cumulative dose of 3.0 mJ/cm$^2$ that may be sufficient for a user having Type I or Type II skin to synthesize an adequate amount of daily vitamin-D. In embodiments, when UV-B exposure is active, the apparatus may provide a signal, such as an indicator light or an audible tone, to indicate the presence of UV light such as to discourage the user from looking at the light source. A timer circuit in the apparatus may measure the duration of the exposure and automatically disable UV-B light generation once a predefined time period for delivering an appropriate cumulative dose has elapsed.

In this example, during the shower time, IR light may be provided for skin rejuvenation and visible light may be provided as a circadian stimulus. For example, the apparatus may deliver two different bands of IR light, e.g., 830 nm and 650 nm, that are known to promote skin healing but that may not be readily absorbed by water. Delivering 50 mW/cm$^2$ of optical power to the skin for a 5 minute exposure leads to a cumulative dose of 15 J/cm$^2$ that may improve the feeling and appearance of skin. This infrared exposure may also provide the feeling of warmth and comfort to the user in the shower. The total dose of infrared light may be limited by a timer, a user command, or the time a user spends in the shower (e.g., with an automatic shut-off after inactivity is detected) as there is little risk from the skin receiving too much IR light so long as intensities remain sub-thermal, i.e., below 200 mW/cm$^2$.

In embodiments, the apparatus may deliver, at the same time, visible light in the range of, e.g., 500 lux to 40,000 lux that may comprise a combination of wavelengths that may be determined, at least in part, by the time of day. In embodiments, the spectral power distribution of the visible light may be automatically adjusted, e.g., according to the time-of-day to match natural light or according to a user selection (e.g., stimulating vs. relaxation mode) or to achieve a desired aesthetic effect. As an example, in the morning, the apparatus may automatically provide blue-rich visible light that has more than 10% of its optical power in a range of wavelength from 460 nm to 490 nm. Conversely, in the evenings, the apparatus may automatically provide visible light that is blue-depleted with less than 2% of its optical power in the range from 460 nm to 480 nm. It is noted that, unlike UV-B or IR light, visible light dose need not to be limited by duration or cumulative dose and, thus, the end of a visible light cycle may be triggered manually by the user, automatically by sensors, or by a timer.

In this particular example, after a user leaves the shower and, thus, the vicinity of the apparatus, the apparatus may generate UV-C light in the range of, e.g., 0.01 to 100 mW/cm$^2$ to disinfect or sterilize the shower area to prevent the growth of mold. In embodiments, the apparatus may use any number of tools to determine when it is safe to activate the UV-C light. Suitable tools may comprise occupancy sensors, or a timer circuit that defines a required elapsed time after a shower and/or the time-of-day for windows of time that can be allotted for UV-C generation. As with other UV-B light, UV-C exposure may be accompanied by a warning indicator, audible tone, or other mechanism that indicate the presence of UV-C light. Real-time sensors may also be used to turn off UV-C light, e.g., once a motion detector or other input suggests the presence of people or animals in or near the shower.

In embodiments, optical power intensity and total UV-C dose to achieve a desired level of disinfection may be computed considering geometry and reflectivity of the surroundings. Sensor inputs, such as proximity and reflectivity measurements, may be used to automatically adjust exposure levels, as appropriate, e.g., incorporating estimates based on "typical" shower installations. In embodiments, UV-C exposure may be adjusted to ensure more than 99% of SARS-CoV-2 and other viruses and bacteria are neutralized on shower surfaces, on clothing, and other to-be-sterilized objects.

Figure 13:
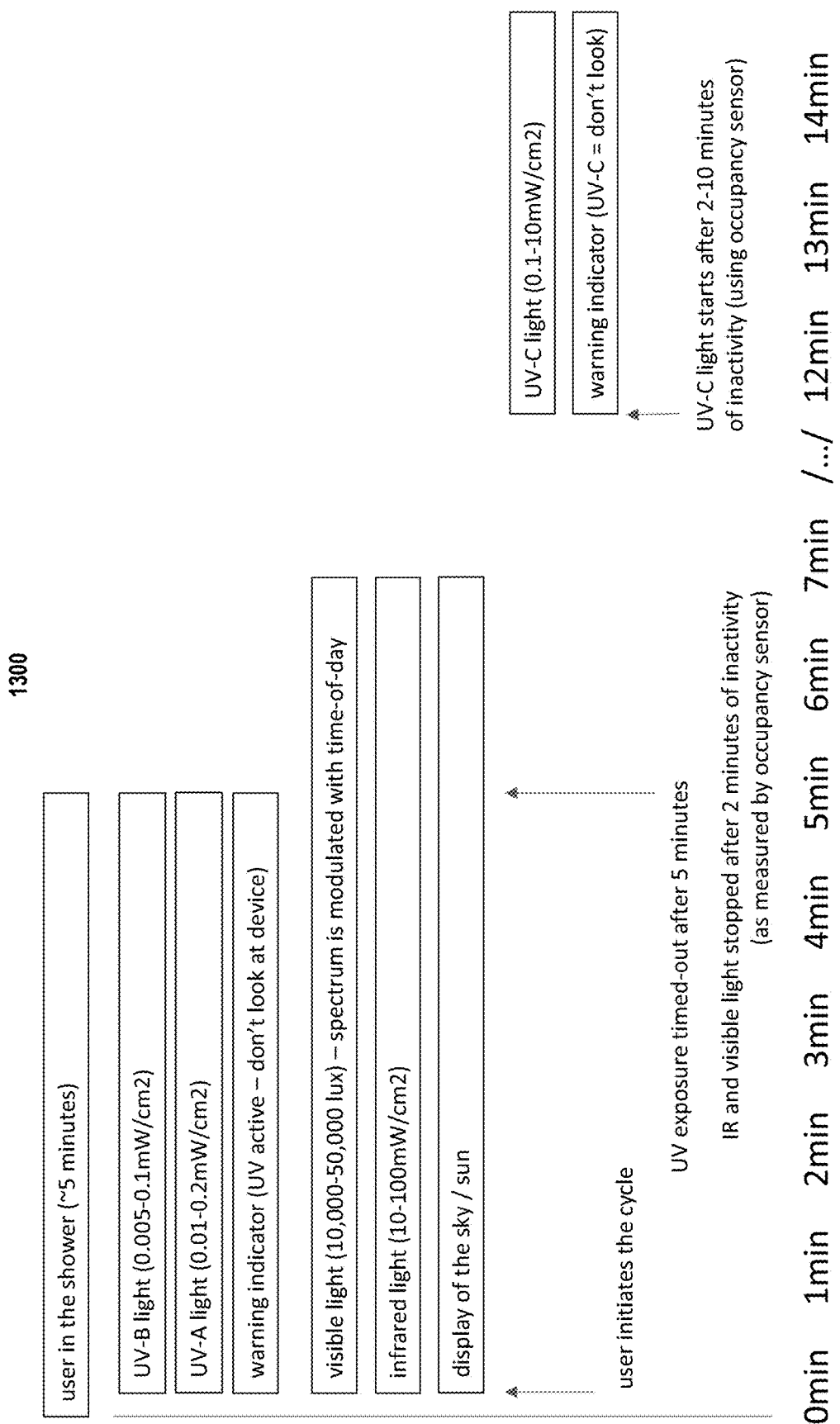
FIG. 13 illustrates components of an exemplary light recipe that simulates the experience and benefits of an outdoor shower according to various embodiments of the present disclosure.

FIG. 13 illustrates components of an exemplary light recipe that simulates the experience and benefits of an outdoor shower according to various embodiments of the present disclosure. In this example, an apparatus mounted at a ceiling may deliver bright visible daylight (5,000 lux to 40,000 lux) having a spectral power distribution that mimics natural light and may vary with the time of day, time of year, and that may further mimic a particular location on earth. For example, during the day, the apparatus may deliver bright blue-rich light, while in early morning or late afternoon, the apparatus may deliver light that mimics a sunrise or sunset, respectively. In embodiments, different spectral power distributions may provide profoundly different aesthetic experiences for the user, with the red-rich light of sunrise or sunset highlighting skin tones, and blue-rich light of the daylight emphasizing fine details and eye color. In a similar manner, some embodiments may mimic both visible and non-visible UV and IR spectral power distributions of natural light. In such embodiments, the red-rich visible light of a sunrise or sunset may be paired with strong IR light little or no UV light, while the blue-rich visible light of daylight may be paired with both UV and IR light.

In embodiments, the apparatus may generate an image that shows or simulates the sky, e.g., by using an active display element, e.g., an LCD, OLED, or any other display mounted in the ceiling, e.g., by using a high-density mix of LEDs. In embodiments, the apparatus may generate an image of the sky, e.g., using a sub-mm light source in a micro/mini-LED display, and the apparatus may use those same or similar elements to deliver, a combination of wavelengths and intensities at deliver therapeutic and aesthetic benefits. An exemplary image may show a blue sky, clouds, sunset, or a sun, which may be static or moving, e.g., to recreate the experience of a skylight. In embodiments, a simulated skylight display may comprise micro-lensing or micro-reflector elements that may allow light sources to deliver light at different/controllable angles to simulate changes in the direct of visible light from the sky.

In embodiments, using the same or separate light sources, either integrated into the same field-of-view as the simulated sky display or separate/adjoining the display-area, the apparatus may simultaneously deliver infrared light to simulate the "heat" of sunlight or rejuvenate the skin, and, for example from a second location, deliver UV-B light to stimulate vitamin-D production, or UV-A and UV-B light for tanning as previously described, e.g., with respect to FIG. 12.

In embodiments, light recipe 1300 in FIG. 13 may recreate the experience of an outdoor shower by using an apparatus that delivers UV-B and UV-A light, e.g., in the range of 0.1 mW/cm$^2$ to 100 mW/cm$^2$ to provide tanning, visible light and IR light. The light may be delivered from a ceiling-mounted apparatus or from wall-mounted apparatus that may create different zones of illumination as previously mentioned with reference to FIG. 4 and FIG. 7A-FIG. 7D.

Similar to the recipe illustrated in FIG. 12, once the simulated outdoor shower experience in FIG. 13 is complete, the apparatus may apply UV-C light to sterilize the area. In short, the ability of the light source and display elements described herein to be controlled individually and used in any combination, enables the apparatus to recreate the flux of an outdoor shower in UV, visible, and infrared wavelength ranges, with the option of including an image of the sky.

Figure 14:
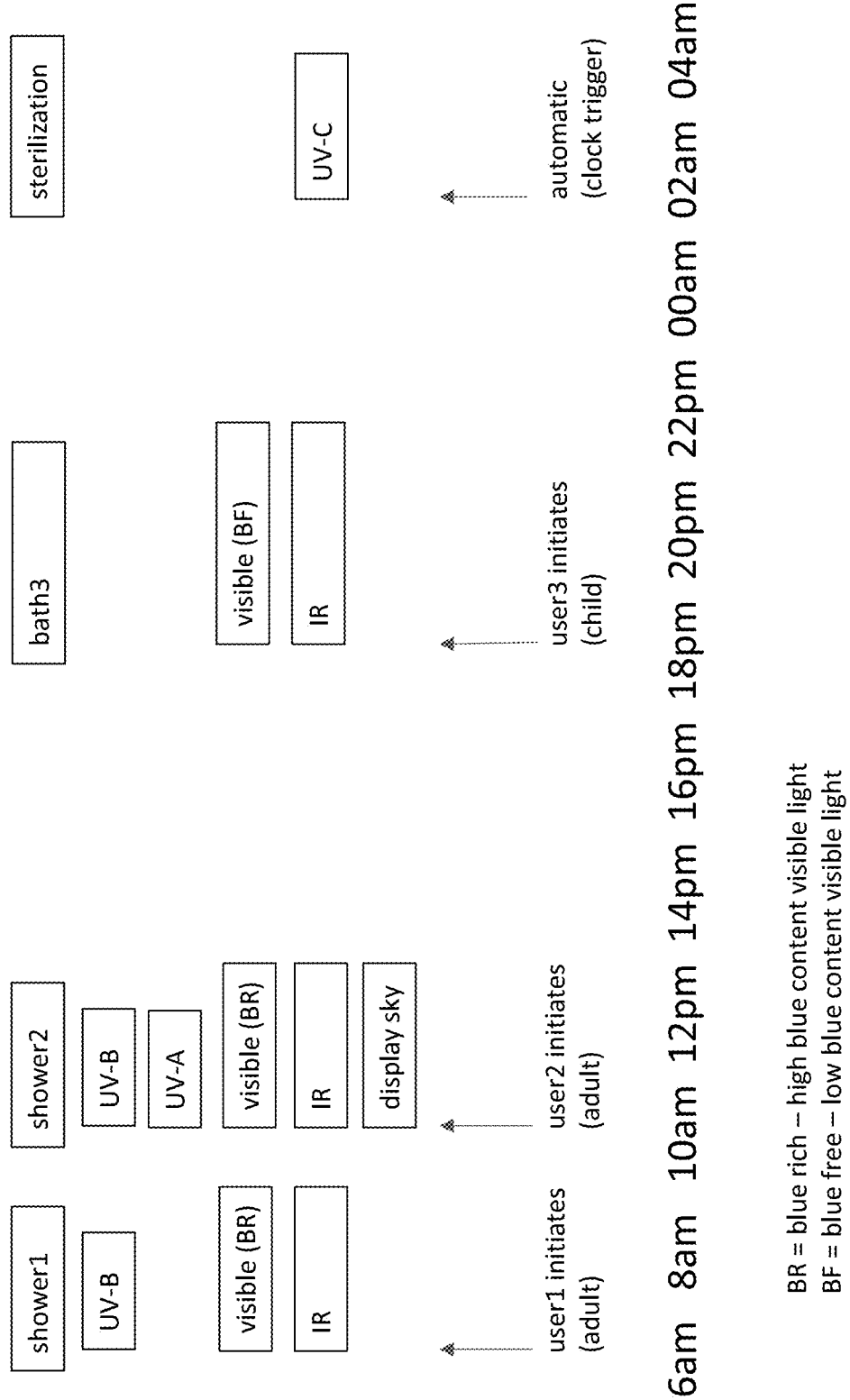
FIG. 14 illustrates components of exemplary light recipes for several users according to various embodiments of the present disclosure.

FIG. 14 illustrates components of exemplary light recipes for several users according to various embodiments of the present disclosure. As depicted, an apparatus may be used over the course of a day with several light recipes that may be triggered by different users, e.g., followed by a sterilization cycle that may be set to occur after midnight. In embodiments, different users may trigger different light recipes, each customized or selected to meet the therapeutic and/or aesthetic needs of the respective user. The example further illustrates how visible light provided by the apparatus may change with the time of day, e.g., with morning showers accompanied by stimulating blue-rich light, while an evening bath may occur in a relaxing blue-free light environment.

In embodiments, UV-C sterilization cycle may be scheduled to occur automatically, e.g., at 2:00 am, when the shower or bathroom is expected to not be in use, or after each use of the shower or bathroom. As previously described, safety interlocks may protect against inadvertent exposure during the UV-C cycle. In embodiments, apparatus may be used to deliver more than one light recipe. Further, a combination of light recipes may be used any time by one user or more users. Furthermore, estimates, algorithms, sensor inputs, and external inputs may be used to automatically generate custom light recipes and automatically trigger and end them in a manner that conveniently requires minimal human interaction.

In embodiments, aspects of the present patent document may be directed to, may include, or may be implemented on one or more computing systems. A computing system may include any instrumentality or aggregate of instrumentalities operable to compute, calculate, determine, classify, process, transmit, receive, retrieve, originate, route, switch, store, display, communicate, manifest, detect, record, reproduce, handle, or utilize any form of information, intelligence, or data. For example, a computing system may be or may include a personal computer (e.g., laptop), tablet computer, phablet, personal digital assistant (PDA), smart phone, smart watch, smart package, server (e.g., blade server or rack server), a network storage device, camera, or any other suitable device and may vary in size, shape, performance, functionality, and price. The computing system may include random access memory (RAM), one or more processing resources such as a central processing unit (CPU) or hardware or software control logic, ROM, and/or other types of memory. Additional components of the computing system may include one or more disk drives, one or more network ports for communicating with external devices as well as various input and output (I/O) devices, such as a keyboard, a mouse, touchscreen and/or a video display. The computing system may also include one or more buses operable to transmit communications between the various hardware components.

Figure 15A:
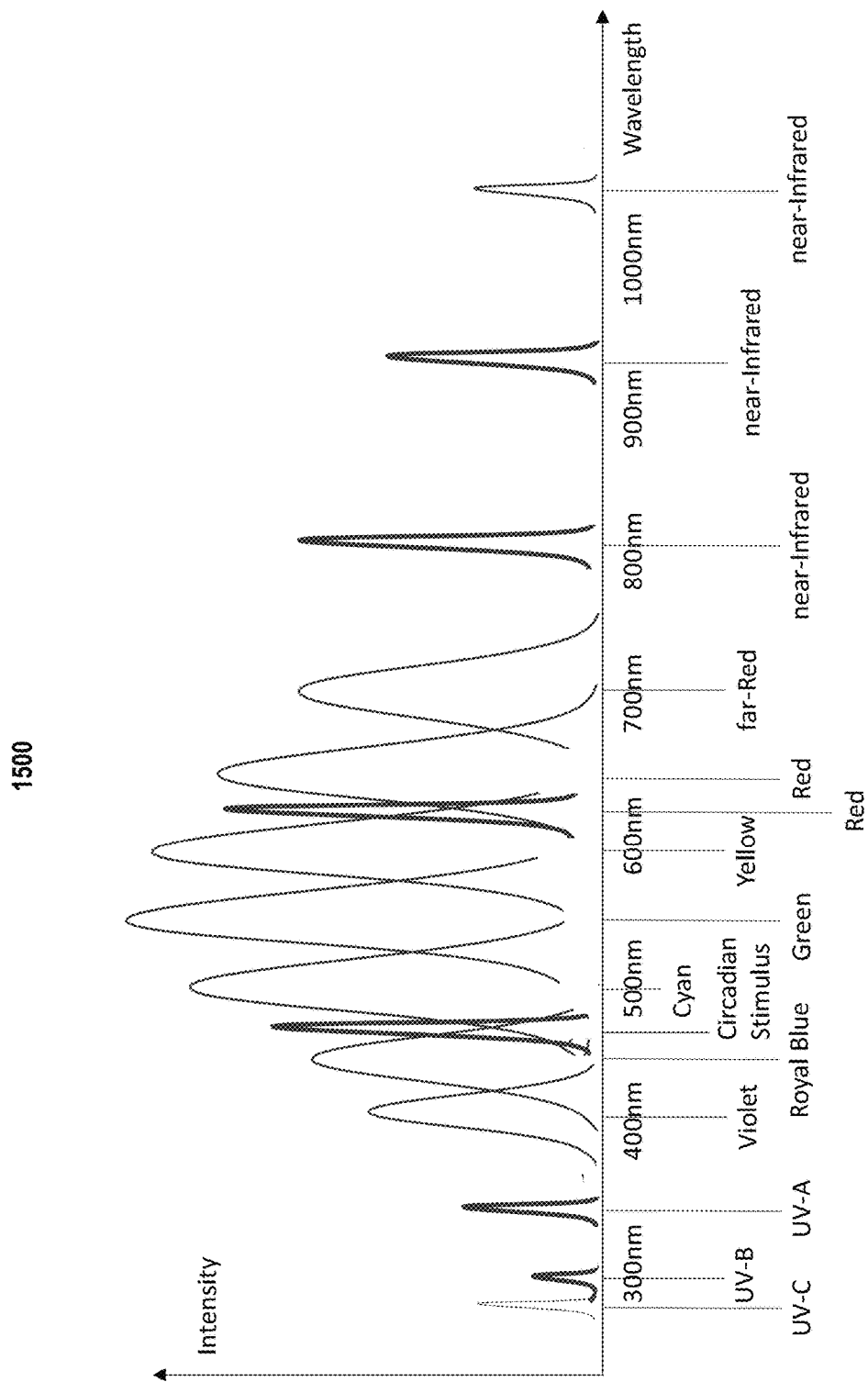
FIG. 15A is an exemplary generated spectral power distribution that simulates natural morning sunlight for delivering therapeutic benefits according to various embodiments of the present disclosure.
Figure 15B:
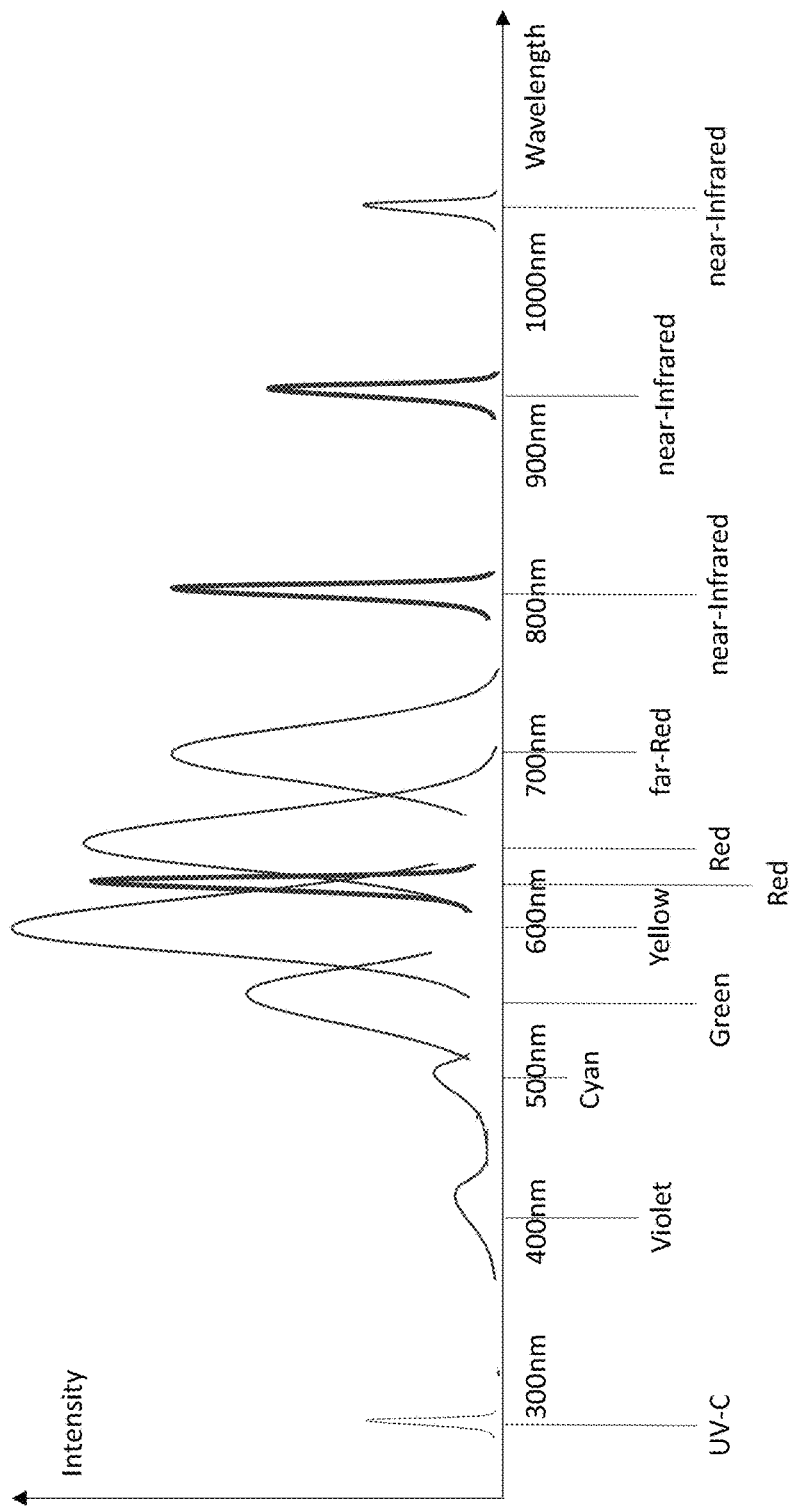
FIG. 15B is an exemplary generated spectral power distribution that simulates natural evening sunlight for delivering therapeutic benefits according to various embodiments of the present disclosure.

FIG. 15A and FIG. 15B are exemplary generated spectral power distributions simulating respective natural morning sunlight and natural evening sunlight for delivering therapeutic benefits according to various embodiments of the present disclosure.

Figure 16A:
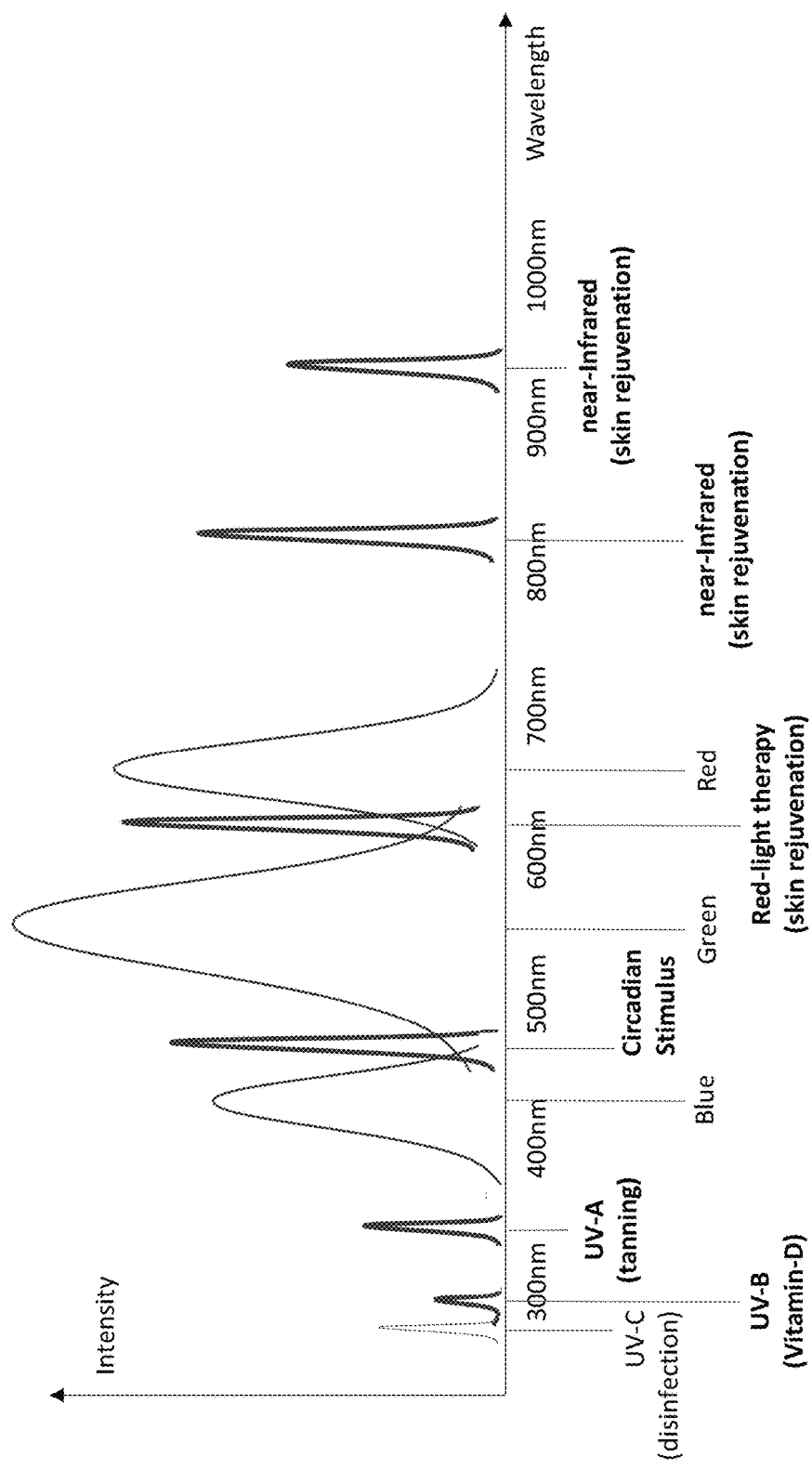
FIG. 16A is an exemplary generated spectral power distribution of unnatural morning light for delivering therapeutic benefits according to various embodiments of the present disclosure.
Figure 16B:
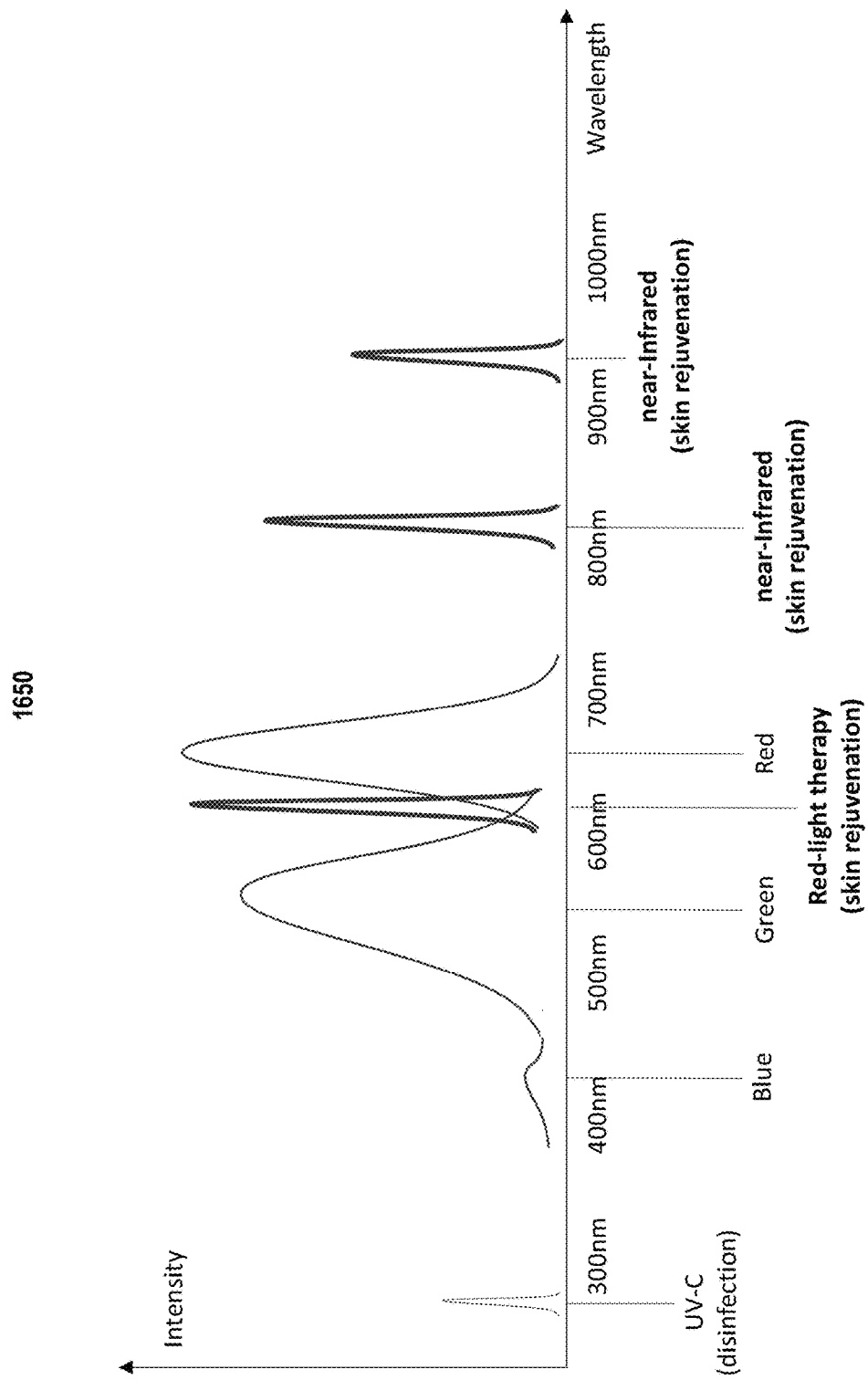
FIG. 16B is an exemplary generated spectral power distribution of unnatural evening light for delivering therapeutic benefits according to various embodiments of the present disclosure.

FIG. 16A and FIG. 16B are exemplary generated spectral power distributions of unnatural morning light and unnatural evening light, respectively, for delivering therapeutic benefits according to various embodiments of the present disclosure.

Figure 17:
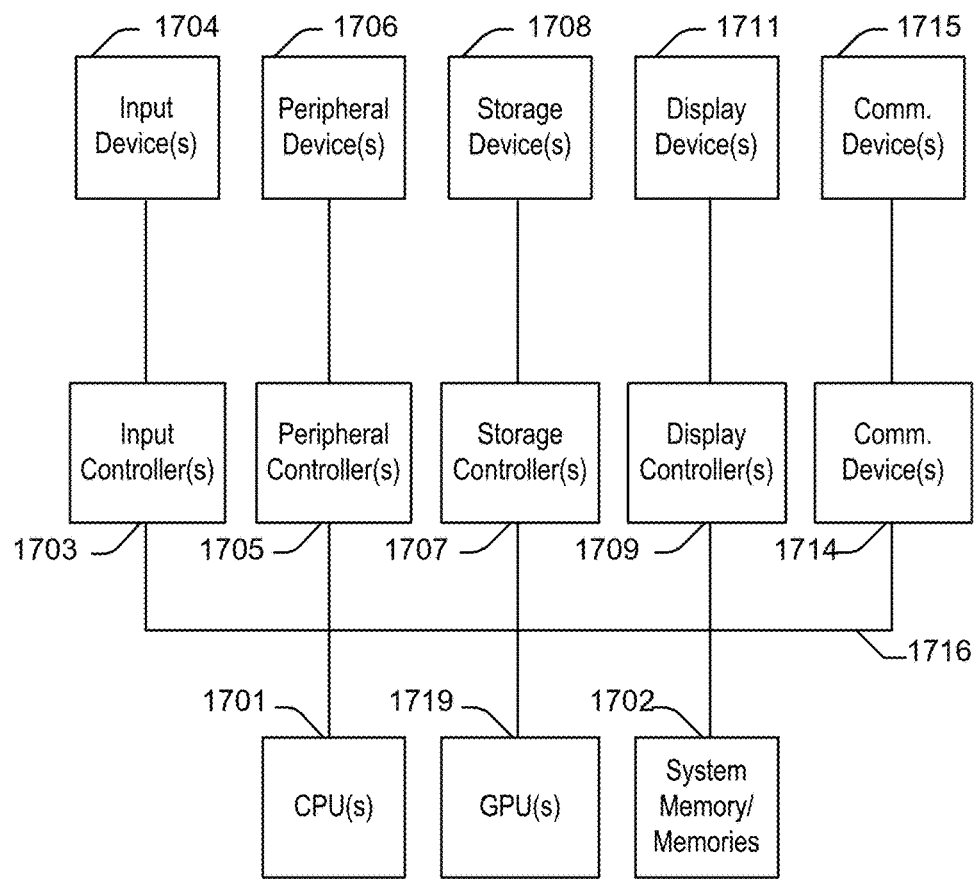
FIG. 17 depicts a simplified block diagram of a computing device, in accordance with embodiments of the present disclosure.

FIG. 17 depicts a simplified block diagram of a computing device/information handling system (or computing system) according to embodiments of the present disclosure. It will be understood that the functionalities shown for system 1700 may operate to support various embodiments of a computing system—although it shall be understood that a computing system may be differently configured and include different components, including having fewer or more components as depicted in FIG. 17.

As illustrated in FIG. 17, the computing system 1700 includes one or more central processing units (CPU) 1701 that provides computing resources and controls the computer. CPU 1701 may be implemented with a microprocessor or the like, and may also include one or more graphics processing units (GPU) 1719 and/or a floating-point coprocessor for mathematical computations. System 1700 may also include a system memory 1702, which may be in the form of random-access memory (RAM), read-only memory (ROM), flash memory, or any combination thereof.

A number of controllers and peripheral devices may also be provided, as shown in FIG. 17. An input controller 1703 represents an interface to various input device(s) 1704, such as a keyboard, mouse, touchscreen, and/or stylus. The computing system 1700 may also include a storage controller 1707 for interfacing with one or more storage devices 1708 each of which includes a storage medium such as magnetic tape or disk, or an optical or electronic medium that might be used to record programs of instructions for operating systems, utilities, and applications, which may include embodiments of programs that implement various aspects of the present invention. Storage device(s) 1708 may also be used to store processed data or data to be processed in accordance with the invention. The system 1700 may also include a display controller 1709 for providing an interface to a display device 1711, which may be a cathode ray tube (CRT), a thin film transistor (TFT) display, organic light-emitting diode, electroluminescent panel, plasma panel, or other type of display. The computing system 1700 may also include one or more peripheral controllers or interfaces 1705 for one or more peripherals 1706. Examples of peripherals may include one or more printers, scanners, input devices, output devices, sensors, and the like. A communications controller 1714 may interface with one or more communication devices 1715, which enables the system 1700 to connect to remote devices through any of a variety of networks including the Internet, a cloud resource (e.g., an Ethernet cloud, an Fiber Channel over Ethernet (FCoE)/Data Center Bridging (DCB) cloud, etc.), a local area network (LAN), a wide area network (WAN), a storage area network (SAN) or through any suitable electromagnetic carrier signals including infrared signals.

In the illustrated system, all major system components may connect to a bus 1716, which may represent more than one physical or virtual bus. However, various system components may or may not be in physical proximity to one another. For example, input data and/or output data may be remotely transmitted from one physical location to another. In addition, programs that implement various aspects of the invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Aspects of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present invention may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It will be appreciated to those skilled in the art that the preceding examples and embodiments are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure. It shall also be noted that elements of any claims may be arranged differently including having multiple dependencies, configurations, and combinations.

What is claimed is:

1. A method for generating and delivering light in an environment where a relatively large portion of a person's skin is exposed, the method comprising:
    receiving an input that is based on a user preference;
    based on the input, determining a set of parameters that control at least one of a wavelength, a flux, or an exposure time of light;
    providing the set of parameters to a light source that is located in at least one of a sauna or a shower to generate light that comprises one or more spectra of natural sunlight and a spectral power distribution that is not present in natural sunlight; and
    controlling the light source to simultaneously deliver the light to at least two of:
        a first zone of illuminance comprising a person's skin to alter a first condition related to light-induced reaction involving one or more layers of the person's skin;
        a second zone of illuminance comprising the eyes of a person to alter a biological process in the person's body; or
        a third zone of illuminance comprising a surface in the environment to at least partially disinfect the surface to reduce growth of at least one of a bacterium, a virus, or a fungus, the first, second, and third zones being different from each other.

2. The method of claim 1, wherein determining a set of parameters comprises receiving input data from one or more sensors, the input data comprising at least one of a distance, information about a skin type, information about skin condition, and a surface reflectivity.

3. The method of claim 1, wherein controlling comprises controlling ultraviolet light associated with at least one of a first flux, infrared associated with a second flux, and visible light associated with a third flux.

4. The method of claim 1, wherein the set of parameters corresponds to one or more effects associated with a condition of at least one of the skin, the eye, or the surface.

5. The method of claim 4, wherein controlling comprises offsetting, among the one or more effects, a first effect caused by a first set of wavelengths with a second effect caused by a second set of wavelengths.

6. The method of claim 4, wherein the condition comprises a physiological response that comprises at least one of a vitamin-D production, a regenerative skin process, or a circadian response.

7. The method of claim 1, wherein disinfecting comprises reducing the growth of a coronavirus that causes Covid-19.

8. The method of claim 1, wherein the light source comprises:
    one or more LEDs that generate the one or more spectra of natural sunlight and the spectral power distribution; and
    one or more optics that generate one or more of the zones of illuminance, the one or more zones of illuminance being independently controlled to cause different effects.

9. The method of claim 1, further comprising adjusting the flux to according to at least one of an atmospheric absorption or a photon energy of a chemical reaction.

10. An apparatus for generating and delivering light in an environment where a relatively large portion of a person's skin is exposed, the apparatus comprising:
    an interface to receive an input that is based on a user preference;
    a light source located in at least one of a sauna or a shower, the light source generating light that comprises one or more spectra of natural sunlight and a spectral power distribution that is not present in natural sunlight; and
    a controller that, in response to receiving input data from one or more sensors, performs steps comprising:
        determining a set of parameters associated with at least one of a wavelength, a flux, or an exposure time of light;
        providing the set of parameters to the light source to generate the light; and
        controlling the light source to simultaneously deliver the light to at least two of:
            a first zone comprising a person's skin to alter a condition related to light-induced reaction involving one or more layers of the person's skin;
            a second zone of illuminance comprising the person's eyes to alter a biological process in the person's body; or
            a third zone of illuminance comprising a surface in the environment to at least partially disinfect the surface to reduce growth of at least one of a bacterium, a virus, or a fungus, the first, second, and third zones being different from each other.

11. The apparatus of claim 10, further comprising one or more optics that generate one or more of the zones of illuminance, the one or more zones of illuminance being independently controlled to cause different effects.

12. The apparatus of claim 10, wherein the light delivered to one of the zones comprises at least one wavelength that is different than that delivered to another zone.

13. The apparatus of claim 10, wherein the controller operates the light source in at least one of a continuous wave mode or a pulse wave mode to adjust, in two or more phases, at least the spectral power distribution.

14. The apparatus of claim 10, wherein the light comprises intensities that correspond to a spectrum of natural light between 280 nm to 320 nm.

15. The apparatus of claim 10, wherein the input data comprises at least one of a distance, information about a skin type, and a surface reflectivity.

16. A system for generating and delivering light in an environment where a relatively large portion of a person's skin is exposed, the system comprising:
    an interface to receive an input that is based on a user preference;
    a light source located in at least one of a sauna or a shower, the light source generating light that comprises one or more spectra of natural sunlight and a spectral power distribution that is not present in natural sunlight;
    one or more sensors that generate sensor data;
    a controller that, in response to receiving the sensor data from the one or more sensors, performs steps comprising:
        determining a set of parameters associated with at least one of a wavelength, a flux, or an exposure time of light;
        providing the set of parameters to the light source to generate the light; and
        controlling the light source to simultaneously deliver the light to at least two of:
            a first zone of illuminance comprising a person's skin to alter a condition related to light-induced reaction involving one or more layers of the person's skin;
            a second zone of illuminance comprising the person's eyes to alter a biological process in the person's body; or
            a third zone of illuminance comprising a surface in the environment to at least partially disinfect the surface to reduce growth of at least one of a bacterium, a virus, or a fungus, the first, second, and third zones being different from each other; and
    one or more optics that generate one or more zones of illuminance, the one or more zones of illuminance being independently controlled to cause different effects.

17. The system of claim 16, wherein reducing growth of the at least one bacterium or virus comprises reducing the growth of a coronavirus that causes Covid-19.

18. The system of claim 16, wherein the controller controls ultraviolet light associated with a first flux, infrared light associated with a second flux, and visible light associated with a third flux.

19. The system of claim 16, wherein at least part of the surface or the one or more optics have a surface reflectivity that at least partially controls one or more of the zones of illuminance.

20. The system of claim 16, further comprising a display that displays an image.

* * * * *